(12) United States Patent
Tomita et al.

(10) Patent No.: US 10,557,131 B2
(45) Date of Patent: Feb. 11, 2020

(54) METHOD OF PRODUCING YEAST EXTRACT

(71) Applicants: National Agriculture and Food Research Organization, Ibaraki (JP); Frontier Engineering Co., Ltd., Tokyo (JP)

(72) Inventors: Satoru Tomita, Ibaraki (JP); Toshihide Nakamura, Ibaraki (JP); Katsuichi Saitou, Ibaraki (JP); Kunihiko Uemura, Ibaraki (JP); Hiroshi Hoshino, Tokyo (JP)

(73) Assignees: National Agriculture and Food Research Organization, Ibaraki (JP); Frontier Engineering Co., Ltd., Tokyo (JP)

( * ) Notice: Subject to any disclaimer, the term of this patent is extended or adjusted under 35 U.S.C. 154(b) by 194 days.

(21) Appl. No.: 15/642,719

(22) Filed: Jul. 6, 2017

(65) Prior Publication Data
US 2018/0010116 A1 Jan. 11, 2018

(30) Foreign Application Priority Data

Jul. 7, 2016 (JP) ................................ 2016-135271
Jun. 20, 2017 (JP) ................................ 2017-120159

(51) Int. Cl.
*C12N 13/00* (2006.01)
*C12N 1/06* (2006.01)
*C12N 1/16* (2006.01)

(52) U.S. Cl.
CPC ............. *C12N 13/00* (2013.01); *C12N 1/063* (2013.01); *C12N 1/16* (2013.01)

(58) Field of Classification Search
None
See application file for complete search history.

(56) References Cited

U.S. PATENT DOCUMENTS

| 6,178,880 B1 * | 1/2001 | Mastwijk | A23L 3/32 |
| | | | 99/358 |
| 2002/0081357 A1 * | 6/2002 | Monch | C12N 1/066 |
| | | | 426/240 |
| 2002/0092773 A1 * | 7/2002 | Goodson | C12M 35/02 |
| | | | 205/341 |
| 2011/0206823 A1 | 8/2011 | Shibuya et al. | |

FOREIGN PATENT DOCUMENTS

| JP | H10-179084 A | 7/1998 |
| JP | 5730579 B2 | 6/2015 |

OTHER PUBLICATIONS

Barsotti et al., "Food Processing by Pulsed Electric Fields. I. Physical Aspects", Food Reviews International, vol. 15, pp. 163-180. (Year: 1999).*

* cited by examiner

*Primary Examiner* — Michelle F. Paguio Frising
(74) *Attorney, Agent, or Firm* — McCormick, Paulding & Huber PLLC

(57) ABSTRACT

A yeast extract is produced by preparing a suspension containing yeast, applying an electric field treatment to the suspension, and then autolyzing the suspension. In this electric field treatment, a voltage to be applied is less than 1000 V/mm, and a temperature of the suspension during an application period of the voltage is 64° C. or less. According to such a production process, a content of amino acids in the yeast extract can be improved. Among amino acids, branched chain amino acids or the like can be efficiently increased.

14 Claims, 15 Drawing Sheets

FIG. 10

| | HIGH ELECTRIC FIELD TREATMENT | LOW ELECTRIC FIELD TREATMENT |
|---|---|---|
| | 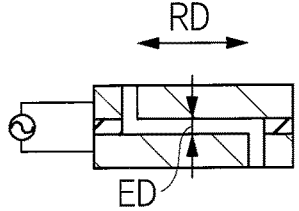 | 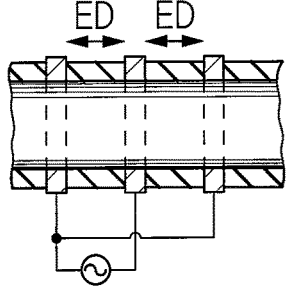 |
| ELECTRODE MATERIAL | Ti(Pt) | Ti(Pt) |
| SIZE OF FLOW PATH (ELECTRIC FIELD TREATMENT UNIT) — CROSS-SECTION | 6mm □ 4mm | 17.5mm |
| SIZE OF FLOW PATH (ELECTRIC FIELD TREATMENT UNIT) — LENGTH | 32mm(RD) | 150mm(2×ED) |
| ELECTRIC FIELD — DISTANCE BETWEEN ELECTRODES (ED) | 4mm | 75mm |
| ELECTRIC FIELD — VOLTAGE BETWEEN ELECTRODES | 600V | 225V |
| ELECTRIC FIELD — VOLTAGE PER 1 mm | 150V/mm (50 TO 500 V/mm) | 3V/mm (3 TO 50 V/mm) |
| ELECTRIC FIELD — FREQUENCY | 20kHz (5 TO 100kHz) | 20kHz (5 TO 100kHz) |
| ELECTRIC FIELD APPLICATION TIME | 0.03 SECOND (0.001 TO 1 SECOND) | 2.5 SECONDS (1 TO 30 SECONDS) |
| TREATMENT MATERIAL | LOW VISCOSITY | APPLICABLE TO HIGH VISCOSITY |

METHOD OF PRODUCING YEAST EXTRACT

CROSS-REFERENCE TO RELATED APPLICATIONS

This application claims priority to Japanese Patent Application Number 2016-135271, filed on Jul. 7, 2016 and to Japanese Patent Application Number 2017-120159, filed on Jun. 20, 2017, each of which is hereby incorporated by reference in its entirety.

TECHNICAL FIELD OF THE INVENTION

The present invention relates to a method of producing a yeast extract, and more specifically, relates to a method of producing a yeast extract in which amino acids are contained at high concentration.

BACKGROUND OF THE INVENTION

A yeast extract is an extract obtained by extracting useful components of yeast. The yeast extract contains amino acids, nucleic acid-related substances, minerals, and vitamins as the main component, and is used in various fields of pharmaceuticals, culture media, foods, feeds, and the like. In particular, in a food production process, a yeast extract is used for improving or enhancing a flavor. Demand for the yeast extract has been increased for its good image of being a natural material, and the production quantity has been increasing year by year.

Various methods such as autolysis method, hydrothermal treatment method, and enzymatic treatment method are used for producing a yeast extract. A yeast autolysate is obtained by autolyzing the cells with digestive enzymes contained in the yeast cells. In this way, proteins constituting yeast are decomposed into amino acids or low-molecular peptide chains having umami taste.

When a yeast extract is produced by such an autolysis method, it is desired to increase the content of the useful components in the extract.

For example, in a production process of a yeast extract, autolysis can be promoted by adding toluene, ethyl acetate, an inorganic acid, or the like. In addition, a method of promoting autolysis is as follows.

For example, in Japanese Patent Application Laid-Open Publication No. H10-179084 (Patent Document 1), disclosed is a technique in which, in producing a yeast extract by the autolysis method, the first stage of enzyme reaction is performed at the optimal reaction temperature at which an enzyme among the proteases contained in yeast is more actively reacted in a low temperature range, subsequently, the second stage of enzyme reaction is performed at a temperature higher than the optimal reaction temperature and in the temperature range in which propagation of bacteria is suppressed, or higher, and further the third stage or more of enzyme reactions with different enzyme reaction temperatures are performed.

In addition, in Japanese Patent No. 5730579 (Patent Document 2), disclosed is a method of producing yeast highly containing amino acids in which yeast in the stationary phase of growth is cultured under the condition that the pH of the liquid medium is 7.5 or more and less than 11. In this way, yeast highly containing amino acids can be obtained.

SUMMARY OF THE INVENTION

As described above, when a yeast extract is produced by the autolysis method, it is desired to increase the useful components in the extract.

However, addition of chemicals to promote autolysis of yeast ruins the image of being a natural material. Further, when a yeast extract is used for foods, it is required to remove residual chemicals, or to restrict the chemicals to be used. Moreover, in a method of adjusting temperature and pH, it takes time and cost to perform pretreatment and condition control.

Accordingly, development of a method of producing a yeast extract, which is performed as quickly and simply as possible, and is easy to control conditions, is desired.

An object of the present invention is to provide a method of producing a yeast extract, which is performed in a short period of time and in a short process and is easy to control conditions. In particular, an object of the present invention is to provide a method of producing a yeast extract containing useful components such as amino acids at high concentration.

A method of producing a yeast extract according to the present invention, includes the steps of: (a) preparing a suspension containing yeast; (b) applying an electric field treatment to the suspension; and (c) after the step (b), autolyzing the yeast in the suspension.

In the step (b) described above, a voltage (a voltage per 1-mm gap between the electrodes between which the suspension flows) to be applied is less than 1000 V/mm, and a temperature of the suspension during an application period of the voltage is 64° C. or less.

In the step (b) described above, a voltage to be applied is 3 V/mm or more to 150 V/mm or less.

In the step (b) described above, an application time of the voltage is less than 25 seconds.

In the step (b) described above, a voltage to be applied is an alternating current (AC) voltage.

The yeast described above belongs to genus *Saccharomyces* or genus *Candida*.

As described above, by applying an electric field treatment to a suspension containing yeast, a content of amino acids in a yeast extract can be improved.

BRIEF DESCRIPTIONS OF THE DRAWINGS

FIG. 10 is a diagram summarizing an example of use conditions of the high and the low electric field devices;

DESCRIPTIONS OF THE PREFERRED EMBODIMENTS

First Embodiment

Hereinafter, embodiments of the present invention will be described in detail with reference to the drawings.

(Enrichment of Amino Acid Content in Autolyzed Yeast Extract by Electric Field Treatment)

Figure 1:
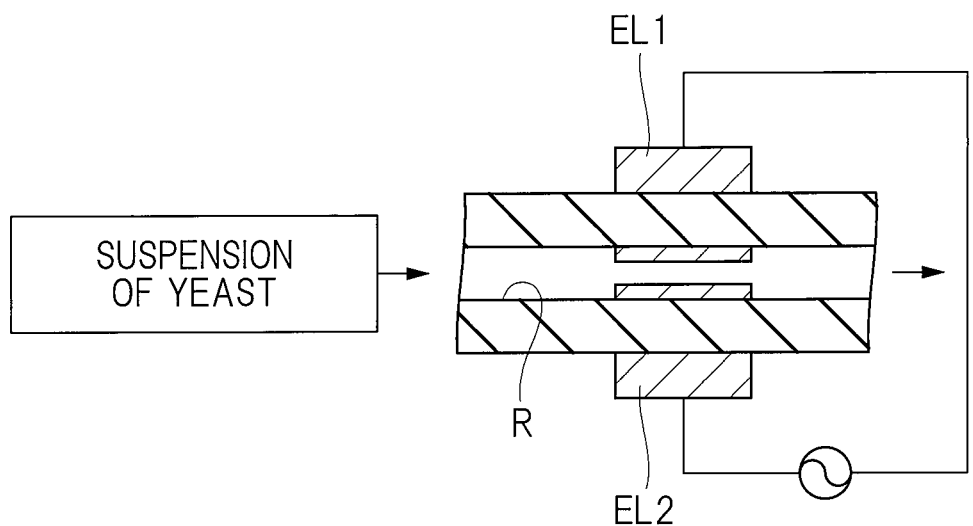
FIG. 1 is a schematic longitudinal-section view showing an electric field treatment process among production processes of a yeast extract.

FIG. 1 is a schematic longitudinal-section view showing an electric field treatment process among production processes of a yeast extract. As shown in FIG. 1, a suspension of yeast is flowed into a flow path R made of an electrical insulating material. For example, genus *Saccharomyces*, genus *Candida*, or the like can be used as the yeast materials. As a liquid for a suspension, for example, water (pure water, or ion-exchange water) can be used. A concentration of yeast in the suspension is, for example, substantially several percent to several tens of percent (w/v).

A pair of the electrodes EL1 and EL2 facing each other at a narrow gap (for example, substantially 0.1 to 5 mm) is arranged in the middle of the flow path R. An AC voltage having a frequency of, for example, substantially 5 kHz to 20 kHz is applied to between the electrodes EL1 and EL2 at substantially 150 V per 1-mm gap between the electrodes EL1 and EL2. For example, a flow rate of the suspension is controlled by a pump, and passage time of the suspension between the electrodes EL1 and EL2 is, for example, 0.1 second or less.

As described above, the suspension of yeast to which the electric field treatment has been applied between the electrodes EL1 and EL2 is cooled and then, heated for several hours, for example, in a thermostat bath at 40° C. to 50° C. In this way, the suspension of yeast is autolyzed. The expression "autolysis" means that cells of yeast are decomposed through the action of its own digestive enzymes. For example, proteins constituting yeast are decomposed into amino acids or low-molecular peptide chains having umami taste.

(Enrichment of Amino Acid Content in Autolyzed Yeast Extract by Short-Time Heat Treatment)

Figure 2:
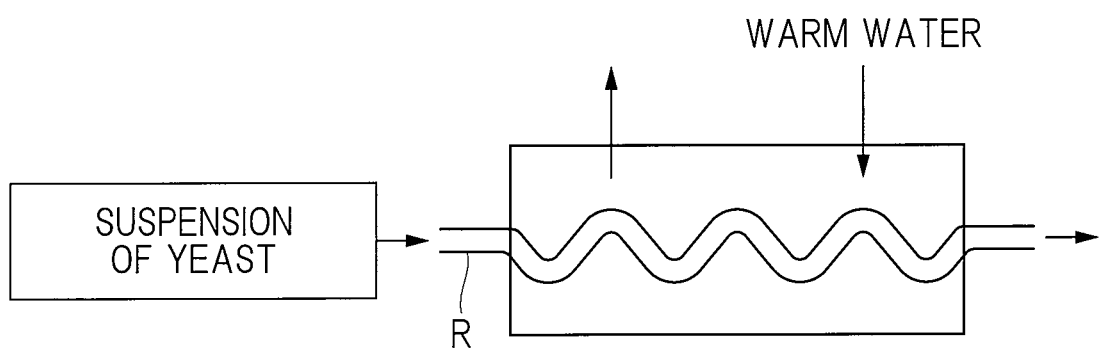
FIG. 2 is a schematic longitudinal-section view showing a short-time heat treatment process among the production processes of the yeast extract.

FIG. 2 is a schematic longitudinal-section view showing a short-time heat treatment process among the production processes of the yeast extract. As shown in FIG. 2, a suspension of yeast is flowed into the flow path R made of an electrically insulating material. For example, genus *Saccharomyces*, genus *Candida*, or the like can be used as the yeast materials. As a liquid for the suspension, for example, water can be used. A concentration of yeast in the suspension is, for example, substantially several percent (w/v).

At midpoint of the flow path R, a heat exchanger is inserted. The suspension of yeast can be heated with the heat exchanger. A heating temperature is, for example, substantially 50° C. to 60° C. In addition, a flow rate of the suspension is controlled by a pump or the like, passage time of the heat exchanger is, for example, substantially several seconds, and during the several seconds, the suspension of yeast can be heated up to the above-described 50° C. to 60° C.

As described above, the suspension of yeast to which a short-time heat treatment has been applied is cooled and then, heated for several hours, for example, in the thermostat bath at 40° C. to 50° C. In this way, the suspension of yeast is autolyzed.

Example 1

(Test A)

Commercially-available dry yeast (*Saccharomyces cerevisiae*) (*Saccharomyces cerevisiae*) was suspended in ion-exchanged water at a final concentration of 5% (w/v). After standing for six hours, the suspension of yeast was used for electric field treatment. Next, a high electric field (high AC electric field) of 20 kHz and 150 V/mm was applied for 0.03 s to the suspension of yeast. Application time of this high electric field corresponds to passage time of the suspension between the electrodes. Specifically, the suspension was allowed to pass through between the electrodes having a 4-mm gap between the electrodes, a voltage of 600 V was applied between the electrodes, and the suspension was allowed to pass through between the electrodes in 0.03 s. The temperature of the suspension was increased up to 54° C. after the application of the electric field. This suspension was cooled down to 7° C. with the heat exchanger, and then, the cooled suspension was incubated at 45° C. for six hours to perform the autolysis of yeast.

The suspension of yeast (yeast liquid) after the autolysis was heated at 80° C. to stop the yeast reaction. After that, free amino acid analysis in the yeast liquid was performed.

(Test B)

As control 1, commercially-available dry yeast was suspended in water so as to be 5% (w/v), and the resultant suspension was left for six hours. Then, the suspension was incubated at 45° C. for six hours to perform the autolysis of yeast as in the case of Test A described above. The suspension of yeast (yeast liquid) after the autolysis was heated at 80° C. to stop the yeast reaction. After that, free amino acid analysis in the yeast liquid was performed.

(Test C)

As control 2, commercially-available dry yeast was suspended in water so as to be 5% (w/v), and the resultant suspension was left for six hours. Then, the suspension was allowed to pass through between electrodes without applying the electric field, and the resultant suspension was incubated at 45° C. for six hours to perform the autolysis of yeast as in the case of Test A described above. The suspension of yeast (yeast liquid) after the autolysis was heated at 80° C. to stop the yeast reaction. After that, free amino acid analysis in the yeast liquid was performed.

(Test D)

In the electric field treatment of Test A described above, the temperature rise of the suspension of yeast was confirmed, and therefore, the short-time heat treatment using the heat exchanger was performed. The 5% (w/v) suspension of yeast was left for six hours, allowed to pass through the heat exchanger, and heated up to 54° C. in 8.3 s. This suspension was cooled down to 7° C. with the heat exchanger as in the case of Test A described above, and then, the cooled suspension was incubated at 45° C. for six hours to perform the autolysis of yeast. The suspension of yeast (yeast liquid) after the autolysis was heated at 80° C. to stop the yeast reaction. After that, free amino acid analysis in the yeast liquid was performed.

The results of the free amino acid analysis in Tests A to D described above are indicated in Tables 1 to 4. Note that, with respect to the suspension in each of Tests A to D, the suspension before autolysis, that is, the suspension with an incubation time of zero hour was also subjected to the free amino acid analysis.

The following Table 1 indicates results of the free amino acid analysis of the high electric field treatment (indicated as "electric field 150 V/mm" or "HEF150") in Test A described above. The expression of 0 h indicates the sample did not autolyze (before autolysis), and the expression of 6 h indicates the sample autolyzed for six hours (after autolysis) (the same applies also to the following Tests B to D). Table 2 indicates results of the free amino acid analysis of control 1 (indicated as "control" or "CON") in Test B described above. Table 3 indicates results of the free amino acid analysis of control 2 (indicated as "in-system passage" or "HEF000") in Test C described above. Table 4 indicates results of the free amino acid analysis of the short-time heat treatment using the heat exchanger (indicated as "heat exchanger" or "PHE") in Test D described above. Note that, in the Table, "ND" indicates "below the detection limit." In addition, in each table, the relation between the numbers (No.), and the abbreviations and the amino acid names (partly including those other than amino acids) are as follows:

1. P-Ser: Phosphoserine
2. Tau: Taurine
3. PEA: Phosphoethanolamine
4. Urea: Urea
5. Asp: Aspartic acid
6. Thr: Threonine
7. Ser: Serine
8. Asn: Asparagine
9. Glu: Glutamic acid
10. Gln: Glutamine
11. Sar: Sarcosine
12. AAA: Aminoadipic acid
13. Gly: Glycine
14. Ala: Alanine
15. Cit: Citrulline
16. a-ABA: α-Aminobutyric acid
17. Val: Valine
18. Cys: Cysteine
19. Met: Methionine
20. Cysta: Cystathionine
21. Ile: Isoleucine
22. Leu: Leucine
23. Tyr: Tyrosine
24. b-Ala: β-Alanine
25. Phe: Phenylalanine
26. b-ABA: β-Aminobutyric acid
27. GABA: Gamma-aminobutyric acid
28. MEA: Monoethanolamine
29. $NH_3$: Ammonia
30. Hyli-1: Hydroxylysine-1
31. Orn: Ornithine
32. 1M-His: 1-Methylhistidine
33. His: Histidine
34. Lys: Lysine
35. 3M-His: 3-Methylhistidine
36. Trp: Tryptophan
37. Ans: Anserine
38. Car: Carnosine
39. Arg: Arginine
40. Hypro: Hydroxyproline
41. Pro: Proline

TABLE 1

| No. | Peak name | Electric field 150 V/mm | |
|---|---|---|---|
| | | HEF 150 0 h | HEF 150 6 h |
| 1 | P-Ser | 2.007 | 2.165 |
| 2 | Tau | ND | ND |
| 3 | PEA | ND | ND |
| 4 | Urea | ND | ND |
| 5 | Asp | 10.535 | 31.794 |
| 6 | Thr | 4.861 | 15.61 |
| 7 | Ser | 7.191 | 19.076 |
| 8 | Asn | 7.199 | 15.658 |
| 9 | Glu | 39.421 | 25.782 |
| 10 | Gln | 11.367 | 18.559 |
| 11 | Sar | ND | ND |
| 12 | AAA | 3.622 | 2.422 |
| 13 | Gly | 4.456 | 10.925 |
| 14 | Ala | 59.857 | 84.824 |
| 15 | Cit | ND | ND |
| 16 | a-ABA | ND | 1.164 |
| 17 | Val | 10.688 | 30.413 |
| 18 | Cys | 12.475 | 10.487 |
| 19 | Met | 1.222 | 7.507 |
| 20 | Cysta | ND | ND |
| 21 | Ile | 6.348 | 21.673 |
| 22 | Leu | 9.403 | 39.705 |
| 23 | Tyr | 5.552 | 19.843 |
| 24 | b-Ala | ND | ND |
| 25 | Phe | 7.609 | 26.013 |
| 26 | b-ABA | ND | ND |
| 27 | GABA | 65.765 | 94.322 |
| 28 | MEA | ND | ND |
| 29 | NH3 | 0.86 | 1.592 |
| 30 | Hylys-1 | ND | ND |
| 31 | Orn | 2.844 | 3.4 |
| 32 | 1M-His | ND | ND |
| 33 | His | 1.258 | 3.828 |
| 34 | Lys | 7.883 | 24.585 |
| 35 | 3M-His | ND | 0.775 |
| 36 | Trp | ND | 7.142 |
| 37 | Ans | ND | ND |
| 38 | Car | ND | ND |
| 39 | Arg | 12.463 | 25.809 |
| 40 | Hypro | ND | ND |
| 41 | Pro | 36.826 | 43.001 |
| | Total | 331.712 | 588.174 |

TABLE 2

| No. | Peak name | Control | |
|---|---|---|---|
| | | CON 0 h | CON 6 h |
| 1 | P-Ser | 1.737 | 1.695 |
| 2 | Tau | ND | ND |
| 3 | PEA | ND | ND |
| 4 | Urea | ND | ND |

TABLE 2-continued

| | | Control | |
|---|---|---|---|
| No. | Peak name | CON 0 h | CON 6 h |
| 5 | Asp | 9.244 | 26.229 |
| 6 | Thr | 4.108 | 11.637 |
| 7 | Ser | 6.078 | 14.004 |
| 8 | Asn | 6.191 | 11.75 |
| 9 | Glu | 39.036 | 25.993 |
| 10 | Gln | 10.1 | 16.239 |
| 11 | Sar | ND | ND |
| 12 | AAA | 3.464 | 1.995 |
| 13 | Gly | 3.667 | 8.573 |
| 14 | Ala | 52.036 | 70.674 |
| 15 | Cit | ND | ND |
| 16 | a-ABA | ND | 0.383 |
| 17 | Val | 8.939 | 22.235 |
| 18 | Cys | 11.396 | 8.064 |
| 19 | Met | 0.999 | 4.976 |
| 20 | Cysta | ND | ND |
| 21 | Ile | 5.406 | 15.588 |
| 22 | Leu | 7.745 | 27.809 |
| 23 | Tyr | 4.683 | 14.321 |
| 24 | b-Ala | ND | ND |
| 25 | Phe | 6.379 | 18.555 |
| 26 | b-ABA | ND | ND |
| 27 | GABA | 54.956 | 76.963 |
| 28 | MEA | ND | ND |
| 29 | NH3 | 0.691 | 1.232 |
| 30 | Hylys-1 | ND | ND |
| 31 | Orn | 2.472 | 3.045 |
| 32 | 1M-His | ND | ND |
| 33 | His | 1.056 | 3.079 |
| 34 | Lys | 6.513 | 19.634 |
| 35 | 3M-His | ND | 0.52 |
| 36 | Trp | ND | 4.863 |
| 37 | Ans | ND | ND |
| 38 | Car | ND | ND |
| 39 | Arg | 10.703 | 20.864 |
| 40 | Hypro | ND | ND |
| 41 | Pro | 32.601 | 37.417 |
| | Total | 290.2 | 468.337 |

TABLE 3

| | | In-system passage | |
|---|---|---|---|
| No. | Peak name | HEF000 0 h | HEF000 6 h |
| 1 | P-Ser | 1.882 | 1.791 |
| 2 | Tau | ND | ND |
| 3 | PEA | ND | ND |
| 4 | Urea | ND | ND |
| 5 | Asp | 9.731 | 27.449 |
| 6 | Thr | 4.495 | 12.042 |
| 7 | Ser | 6.601 | 14.588 |
| 8 | Asn | 6.794 | 12.017 |
| 9 | Glu | 39.665 | 25.442 |
| 10 | Gln | 10.767 | 16.292 |
| 11 | Sar | ND | ND |
| 12 | AAA | 3.94 | 2.268 |
| 13 | Gly | 4.114 | 8.93 |
| 14 | Ala | 56.488 | 73.826 |
| 15 | Cit | ND | ND |
| 16 | a-ABA | ND | 0.991 |
| 17 | Val | 9.81 | 23.023 |
| 18 | Cys | 12.289 | 8.818 |
| 19 | Met | 1.111 | 5.117 |
| 20 | Cysta | ND | ND |
| 21 | Ile | 5.887 | 16.009 |
| 22 | Leu | 8.585 | 29.034 |
| 23 | Tyr | 5.149 | 14.842 |
| 24 | b-Ala | ND | ND |
| 25 | Phe | 7.014 | 19.41 |
| 26 | b-ABA | ND | ND |
| 27 | GABA | 61.196 | 82.754 |

TABLE 3-continued

| | | In-system passage | |
|---|---|---|---|
| No. | Peak name | HEF000 0 h | HEF000 6 h |
| 28 | MEA | ND | ND |
| 29 | NH3 | 0.81 | 1.352 |
| 30 | Hylys-1 | ND | ND |
| 31 | Orn | 2.669 | 3.204 |
| 32 | 1M-His | ND | ND |
| 33 | His | 1.129 | 3.155 |
| 34 | Lys | 7.239 | 19.783 |
| 35 | 3M-His | ND | 0.538 |
| 36 | Trp | ND | 5.561 |
| 37 | Ans | ND | ND |
| 38 | Car | ND | ND |
| 39 | Arg | 11.725 | 21.237 |
| 40 | Hypro | ND | ND |
| 41 | Pro | 35.14 | 38.851 |
| | Total | 314.23 | 488.324 |

TABLE 4

| | | Heat exchanger | |
|---|---|---|---|
| No. | Peak name | PHE54 0 h | PHE54 6 h |
| 1 | P-Ser | 1.235 | 1.855 |
| 2 | Tau | ND | ND |
| 3 | PEA | ND | ND |
| 4 | Urea | ND | ND |
| 5 | Asp | 9.873 | 20.049 |
| 6 | Thr | 1.657 | 14.400 |
| 7 | Ser | 5.259 | 18.597 |
| 8 | Asn | 3.295 | 13.252 |
| 9 | Glu | 162.853 | 57.427 |
| 10 | Gln | ND | 18.274 |
| 11 | Sar | ND | ND |
| 12 | AAA | 3.253 | 6.080 |
| 13 | Gly | 1.096 | 8.837 |
| 14 | Ala | 20.417 | 47.241 |
| 15 | Cit | ND | ND |
| 16 | a-ABA | ND | 1.223 |
| 17 | Val | 6.235 | 27.293 |
| 18 | Cys | 2.591 | 5.502 |
| 19 | Met | ND | 6.438 |
| 20 | Cysta | 0.175 | ND |
| 21 | Ile | 2.849 | 19.910 |
| 22 | Leu | 2.691 | 33.930 |
| 23 | Tyr | 1.376 | 16.151 |
| 24 | b-Ala | ND | ND |
| 25 | Phe | 2.226 | 22.358 |
| 26 | b-ABA | ND | ND |
| 27 | GABA | 2.348 | 65.208 |
| 28 | MEA | ND | ND |
| 29 | NH3 | 0.598 | 0.983 |
| 30 | Hylys-1 | ND | ND |
| 31 | Orn | 2.442 | 2.380 |
| 32 | 1M-His | ND | ND |
| 33 | His | ND | 3.698 |
| 34 | Lys | 4.711 | 22.719 |
| 35 | 3M-His | ND | 0.636 |
| 36 | Trp | ND | 6.596 |
| 37 | Ans | ND | ND |
| 38 | Car | ND | ND |
| 39 | Arg | 7.816 | 22.278 |
| 40 | Hypro | ND | ND |
| 41 | Pro | 32.475 | 35.907 |
| | Total | 277.471 | 499.221 |

Figure 3:
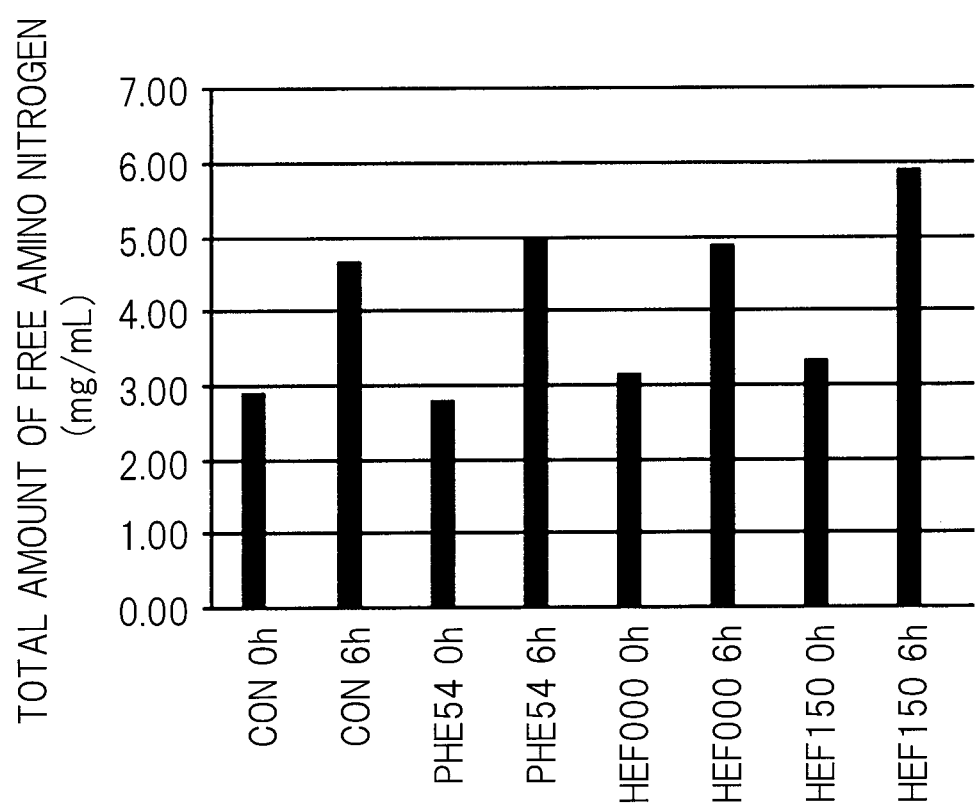
FIG. 3 is a graph of a total amount of amino acids of Tests A to D.

In addition, through the free amino acid analysis of Tests A to D described above, a graph of the total amount of amino acids is shown in FIG. 3. The vertical axis shows the total amount of amino acids (mg/mL). Further, through the free amino acid analysis of Tests A to E described above, a graph of the amount of branched chain amino acids is shown in FIG. 4.

Figure 4:
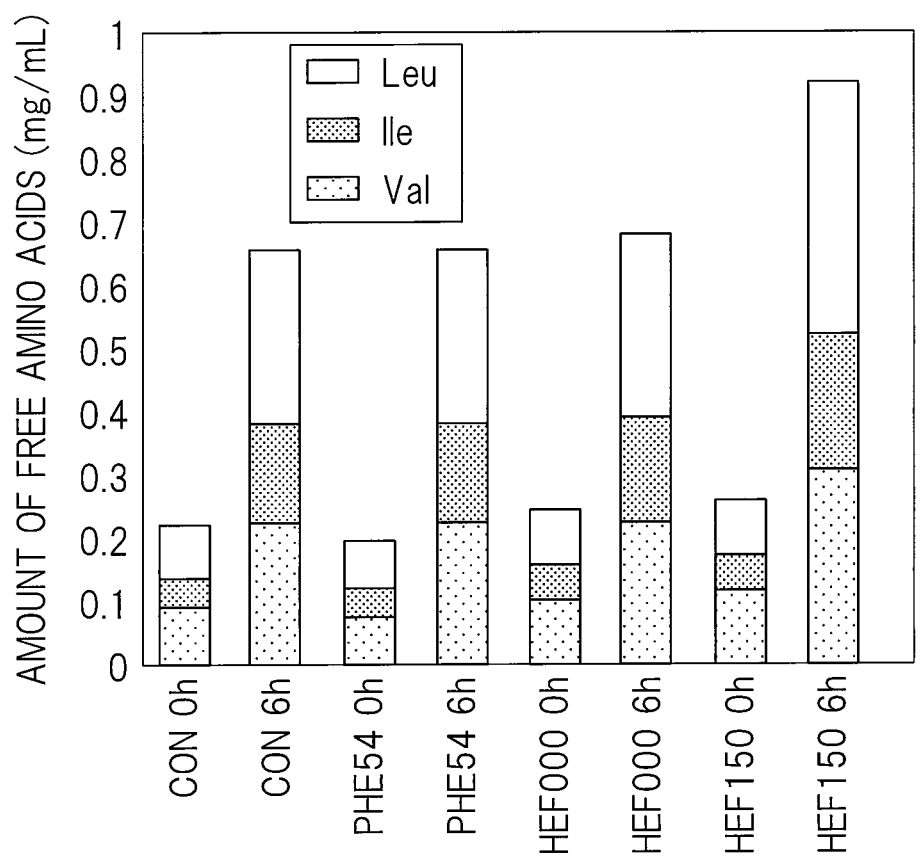
FIG. 4 is a graph of an amount of branched chain amino acids of Tests A to D.

As shown in Tables 1 to 4 and FIGS. 3 and 4, in a case where the high electric field treatment (indicated as "electric field 150 V/mm" or "HEF150") in Test A described above was applied, the total amount of free amino acids was more increased as compared with the cases of control 1 (indicated as "control" or "CON") in Test B described above and of control 2 (indicated as "in-system passage" or "HEF000") in Test C described above. For example, as compared with control 2 (HEF000 6 h), the total amount of free amino acids with an electric field of 150 V/mm (HEF150 6 h) was 1.2 times. Further, this increasing was also observed in a case of non-autolyzed sample. Furthermore, in a case where the high electric field treatment (indicated as "electric field 150 V/mm" or "HEF150") in Test A described above was applied, the total amount of Val (valine), Ile (isoleucine) and Leu (leucine), which are branched chain amino acids, was increased. These branched chain amino acids are essential amino acids in humans, and occupy 35% of the essential amino acids in the muscle protein and occupy 40% of the amino acids required for mammals. For example, as compared with control 2 (HEF000 6 h), the total amount of Val, Ile, and Leu, with an electric field of 150 V/mm (HEF150 6 h) was 1.35 times.

In addition, the amount of all the amino acids analyzed, including the branched chain amino acids (Val, Ile, and Leu), was increased. For example, as compared with control 2 (HEF000 6 h), each amount of the free amino acids with an electric field of 150 V/mm (HEF150 6 h) was increased in all the cases.

Further, from the comparison between Test A and Test D described above, the total amount of free amino acids when the high electric field treatment in Test A had been applied was larger than that when a simple heat treatment as in Test D had been applied. Further, this increasing was also observed in a case of non-autolyzed sample. Furthermore, the total amount of Val, Ile, and Leu, which are branched chain amino acids, was also large. With regard to each amino acid, amino acids other than Glu (glutamic acid) and AAA (amino adipic acid) were increased.

As described above, the amino acid content of the autolyzed yeast extract can be increased by the high electric field treatment or the short-time heat treatment. In particular, in the high electric field treatment described above, a remarkable increase in the free amino acids containing useful free amino acids was able to be confirmed.

As to such an increase in the amino acid content, the possibility that the yeast is electrically activated, the possibility of an effect caused by leakage of an enzyme in a part of yeast by electroporation, or the like is considered, but the factors have not been yet elucidated.

However, it was able to be confirmed that the amino acid content of the autolyzed yeast extract is increased by the high electric field treatment described above, and this is considered to be extremely effective.

According to such a high electric field treatment, addition of chemicals to promote autolysis can be avoided, or an additive amount of chemicals can be reduced, and amino acids capable of being added to foods can be easily produced in a short time and in a short process while maintaining the image of being a natural material.

Herein, in Test A described above, the test was conducted under specific conditions (for example, 150 V/mm), but as shown in Examples 2 and 3 described later, it has been found that the effect is exerted even at 100 V/mm or 50 V/mm.

Accordingly, the high electric field treatment in the present specification indicates the treatment of 50 V/mm or more. However, it is preferred that the voltage per 1-mm gap between the electrodes is less than 1000 V. In a case where the voltage is set to be 1000 V or more, electroporation easily occurs in yeast, and could lead to yeast death. Further, it is preferred that the highest temperature is set to be 64° C. or less during the high electric field treatment. When the temperature exceeds 64° C., the yeast and its digestive enzymes may be inactivated.

Accordingly, it is preferred that the voltage per 1-mm gap between the electrodes is less than 1000 V/mm. Among them, as shown in the present embodiment and Examples 2 and 3 described later, it has been confirmed that, when the high electric field treatment is performed in a range of 50 to 150 V/mm, the amino acid content of the autolyzed yeast extract is increased. Further, an increase of branched chain amino acids has been confirmed.

The treatment time (voltage application time, or voltage application period) of the high electric field treatment can be appropriately adjusted in a range of 0.1 second or less.

In addition, in Example 1 described above, the concentration of yeast in the suspension was set to be 5% (w/v), but not limited this concentration. For example, the concentration of yeast can be adjusted in a range of 1% to 30% (w/v). However, when the concentration of yeast is extremely low, treatment efficiency is lowered. Further, when the concentration of yeast is extremely high, the control of the flow rate may become difficult or variation in application of voltage may be caused. Therefore, it is preferred that the concentration of yeast is adjusted in the range of 1% to 30% (w/v) described above.

Example 2

In Test A of Example 1, a similar experiment was conducted with an electric field of 100 V/mm. In addition, a temperature rise in the suspension of yeast in this case was 29° C., and therefore, in Test B of Example 1, a similar experiment was conducted with the heating by the heat exchanger being set to 29° C. Note that, by using the used suspension of yeast as a control, a similar experiment as in Test C of Example 1 was conducted.

Also in Example 2, in a case where the electric field treatment of Test A is applied, the total amount of amino acids was more increased than that in the case where the heating by the heat exchanger in Test B was applied. Furthermore, each amount of valine, leucine, and isoleucine, which are branched chain amino acids, was increased.

Example 3

In Test A of Example 1, a similar experiment was conducted with an electric field of 50 V/mm. In addition, a temperature rise in the suspension of yeast in this case was 18° C., and therefore, in Test B of Example 1, a similar experiment was conducted with the heating by the heat exchanger being set to 18° C. Note that, by using the used suspension of yeast as a control, a similar experiment as in Test C of Example 1 was conducted.

Also in Example 3, in a case where the electric field treatment in Test A is applied, the total amount of amino acids was more increased than that in the case where the heating by the heat exchanger in Test B was applied. Furthermore, each amount of valine, leucine, and isoleucine, which are branched chain amino acids, was increased.

Example 4

In Test A described above, a high electric field was applied, and electric field treatment with a low electric field was also tested. The 5% (w/v) suspension of yeast was left for six hours, and a low electric field treatment was performed in this suspension of yeast.

As Test E1, a low electric field of 1 V/mm was applied to the suspension of yeast for 25 s. The application time of this electric field corresponds to the passage time of the suspension between the electrodes. Specifically, the suspension was allowed to pass through between the electrodes having a 75-mm gap between the electrodes, a voltage of 75 V was applied between the electrodes, and the suspension was allowed to pass through between the electrodes in 25 s (see FIG. 1). This suspension was cooled down to 7° C. with the heat exchanger, and then, the cooled suspension was incubated at 45° C. for six hours to perform autolysis of yeast.

As Test E2, a low electric field of 3 V/mm was applied to the suspension of yeast for 2.5 s. The application time of this electric field corresponds to the passage time of the suspension between the electrodes. Specifically, the suspension was allowed to pass through between the electrodes having a 75-mm gap between the electrodes, a voltage of 225 V was applied between the electrodes, and the suspension was allowed to pass through between the electrodes in 2.5 s (see FIG. 1). This suspension was cooled down to 7° C. with the heat exchanger, and then, the cooled suspension was incubated at 45° C. for six hours to perform autolysis of yeast.

In Tests E1 and E2 described above, the suspension of yeast (yeast liquid) after autolysis was heated at 80° C. to stop the yeast reaction. After that, free amino acid analysis in the yeast liquid was performed.

The results of the free amino acid analysis in Tests E1 and E2 described above are indicated in Table 5. Table 5 indicates the results of the free amino acid analysis of the low electric field treatment. The Test E1 is indicated as "1S Joule" or "1SJH54." The Test E2 is indicated as "15A Joule" or "15AJH54." Note that, in the table, the relation between the numbers (No.), and the abbreviations and the amino acid names (partly including those other than amino acids) are as described above.

TABLE 5

| No. | Peak name | 15A Joule 15AJH54 6 h | 16 Joule 16JH54 6 h |
|---|---|---|---|
| 1 | P-Ser | 2.385 | 1.984 |
| 2 | Tau | ND | ND |
| 3 | PEA | ND | ND |
| 4 | Urea | ND | ND |
| 5 | Asp | 14.358 | 11.695 |
| 6 | Thr | 13.976 | 11.894 |
| 7 | Ser | 17.571 | 14.661 |
| 8 | Asn | 11.990 | 9.955 |
| 9 | Glu | 58.237 | 44.788 |
| 10 | Gln | 15.466 | 13.364 |
| 11 | Ser | ND | ND |
| 12 | AAA | 8.150 | 6.683 |
| 13 | Gly | 8.858 | 7.508 |
| 14 | Ala | 48.869 | 37.001 |
| 15 | Cit | ND | ND |
| 16 | a-ABA | 1.634 | 1.194 |
| 17 | Val | 26.314 | 21.676 |
| 18 | Cys | 7.238 | 5.688 |
| 19 | Met | 6.174 | 5.022 |
| 20 | Cysta | ND | 0.185 |
| 21 | Ile | 19.319 | 16.172 |
| 22 | Leu | 33.584 | 27.850 |
| 23 | Tyr | 15.790 | 12.832 |
| 24 | b-Ala | ND | ND |
| 25 | Phe | 21.313 | 18.237 |
| 26 | b-ABA | ND | ND |
| 27 | GABA | 56.709 | 48.888 |
| 28 | MEA | ND | ND |
| 29 | NH3 | 0.727 | 0.573 |
| 30 | Hylys-1 | ND | ND |
| 31 | Orn | 2.144 | 1.899 |
| 32 | 1M-His | ND | ND |
| 33 | His | 3.372 | 2.881 |
| 34 | Lys | 21.661 | 18.386 |
| 35 | 3M-His | 0.690 | 0.570 |
| 36 | Trp | 6.615 | 5.328 |
| 37 | Ans | ND | ND |
| 38 | Car | ND | ND |
| 39 | Arg | 21.451 | 18.286 |
| 40 | Hypro | ND | ND |
| 41 | Pro | 36.397 | 30.301 |
| | Total | 480.991 | 395.599 |

Figure 5:
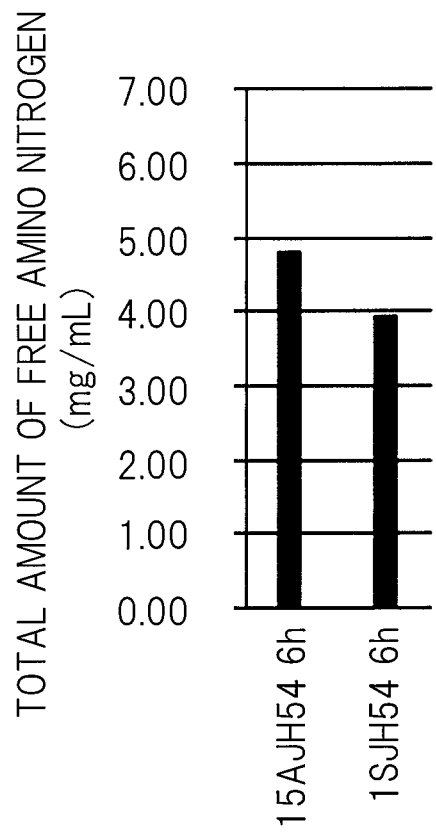
FIG. 5 is a graph of a total amount of amino acids of Tests E1 and E2.

In addition, through the free amino acid analysis of Tests E1 and E2 described above, a graph of the total amount of amino acids is shown in FIG. 5. The vertical axis shows the total amount of amino acids (mg/mL). Further, through the free amino acid analysis of Tests E1 and E2 described above, a graph of the amount of branched chain amino acids is shown in FIG. 6.

Figure 6:
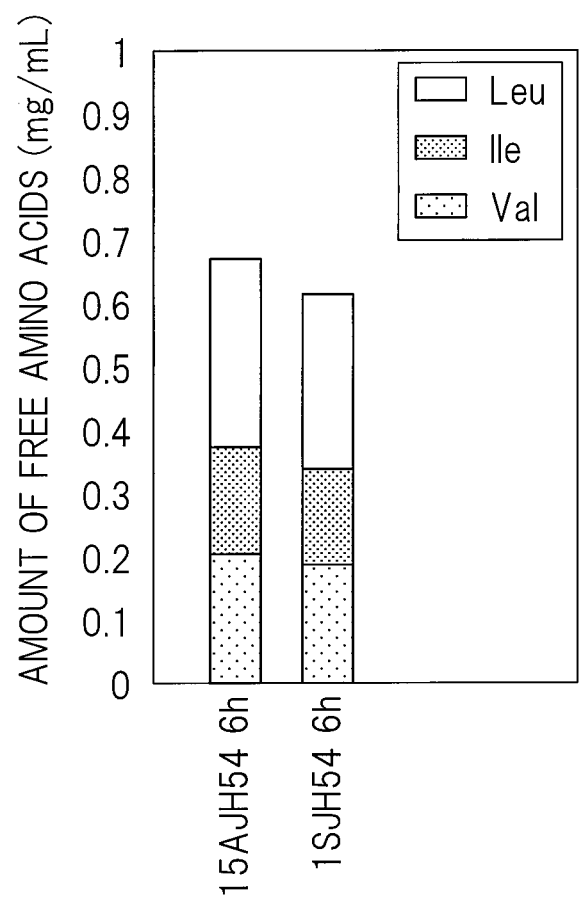
FIG. 6 is a graph of an amount of branched chain amino acids of Tests E1 and E2.

As shown in Table 5 and FIGS. 5 and 6, in a case where the low electric field treatment (indicated as "1S Joule" or "1SJH54") in Test E1 described above was applied, the total amount of free amino acids was almost the same as that in control (not shown) in Example 4. In addition, in a case where the 3-V/mm electric field treatment (15AJH54 6 h) in Test E2 described above was applied, the total amount of free amino acids was more increased as compared with the control (not shown) and Test E1 (1 V/mm applied) described above. Further, the total amount of Val, Ile, and Leu, which are branched chain amino acids, was also increased. Furthermore, the amount of each amino acid was also increased.

As described above, even by the low electric field treatment, in the treatment of 3 V/mm or more, the amino acid content of the autolyzed yeast extract can be increased.

In a case of the low electric field treatment, it is preferred that voltage is applied in a range of 3 V/mm or more to 10 V/mm. Further, it is preferred that the highest temperature is set to be 64° C. or less during the treatment. When the temperature exceeds 64° C., the yeast and its digestive enzymes may be inactivated. The treatment time (voltage application time) can be appropriately adjusted in a range of less than 25 seconds, more preferably 10 seconds or less. In addition, as a method for suppressing the temperature rise of a suspension, there are methods of: 1) increasing a flow rate of a suspension; 2) improving a conductivity of a suspension; and the like.

Further, in a case of the low electric field treatment, the distance between the electrodes can be made longer, and therefore, the suspension at a relatively high concentration can be treated. For example, the concentration of yeast can be adjusted in the range of 1% to 50% (w/v).

Second Embodiment

In the first embodiment, an AC electric field of 150 V/mm or 3 V/mm was applied between the electrodes, but the electric field to be applied may be a pulsed electric field.

Figure 7:
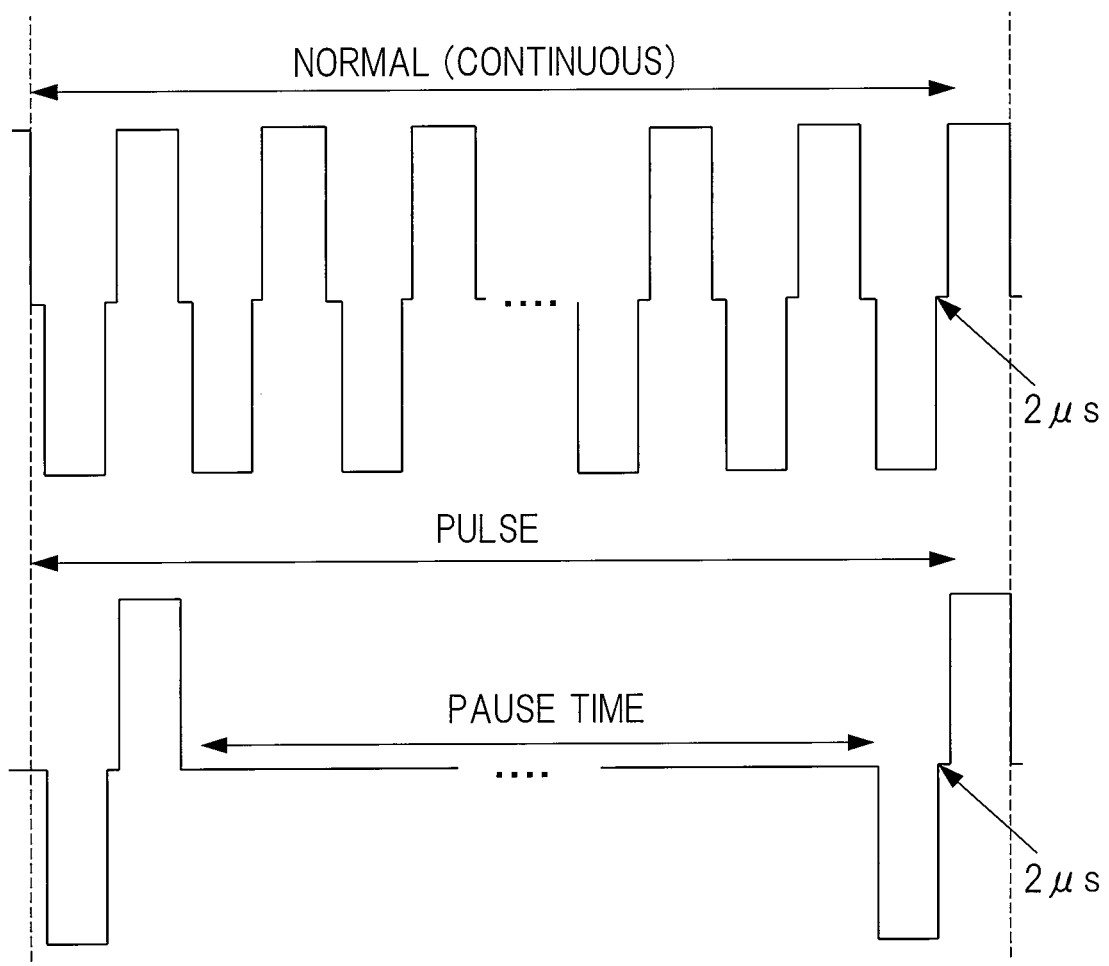
FIG. 7 is a pulse waveform diagram.

FIG. 7 is a waveform diagram of an AC electric field and a pulsed electric field to be applied. Voltage is set to be, for example, 300 V per 1 mm between the electrodes. Frequency can be adjusted, for example, in a range of 5 kHz to 60 kHz. For example, in a case where the frequency of the AC electric field is 21 kHz, the rise time and the fall time (reverse time) of the voltage can be set to 2 μs, and the energizing time (a width of pulse in FIG. 7, that is, periodic time) of the voltage can be set to 22 μs (see the upper part of FIG. 7). As shown in the bottom part of FIG. 7, a pause time may be provided in the energizing time. For example, the pause time can be adjusted in a range of 2 to 6400 μs. Examples of combinations of the frequency and the pulse width of voltage pulses are indicated in Table 6, and an example of the pause time is indicated in Table 7.

TABLE 6

| Frequency (kHz) | Pulse width (μs) |
|---|---|
| 60 | 6.4 |
| 52 | 7.6 |
| 44 | 9.4 |
| 38 | 11.2 |
| 33 | 13.0 |
| 28 | 15.8 |
| 24 | 18.8 |
| 21 | 22.0 |
| 18 | 25.8 |
| 15 | 31.4 |
| 12 | 39.6 |
| 10 | 48.0 |
| 9 | 53.6 |
| 8 | 60.6 |
| 7 | 69.4 |
| 6 | 81.4 |

TABLE 7

| Pause time (μs) |
|---|
| 2 |
| 4 |
| 10 |
| 20 |
| 30 |
| 40 |
| 60 |
| 80 |
| 90 |
| 100 |
| 120 |
| 150 |
| 180 |
| 200 |
| 250 |
| 300 |
| 350 |
| 400 |
| 490 |
| 590 |
| 730 |
| 880 |
| 1080 |
| 1310 |
| 1600 |
| 1950 |
| 2380 |
| 2900 |
| 3530 |
| 4310 |
| 5250 |
| 6400 |

As described above in detail, in the high electric field treatment of the first embodiment, a high voltage pulse (for example, substantially 50 V/mm to 150 V/mm) provided with a pause time in the energizing time may be used. Note that the continuous high voltage pulse treatment without a pause time may be referred to as a high AC electric field treatment in some cases. Further, in the low electric field treatment of the first embodiment, a low voltage pulse (for example, substantially 3 V/mm to 10 V/mm) provided with a pause time in the energizing time may be used.

The frequency can be adjusted, for example, in the range of 5 kHz to 60 kHz.

In addition, as described above, it is preferred that the highest temperature is set to be 64° C. or less during the electric field treatment, and as a method for suppressing a temperature rise of a suspension, there are methods of: 1) increasing a flow rate of a suspension; 2) improving a conductivity of a suspension; and 3) thinning out pulses (providing a pause time) in an AC electric field.

Third Embodiment

There is no limitation on a device used for the electric field treatment described in the first and the second embodiments, but for example, a device described below can be used.

Figure 8:
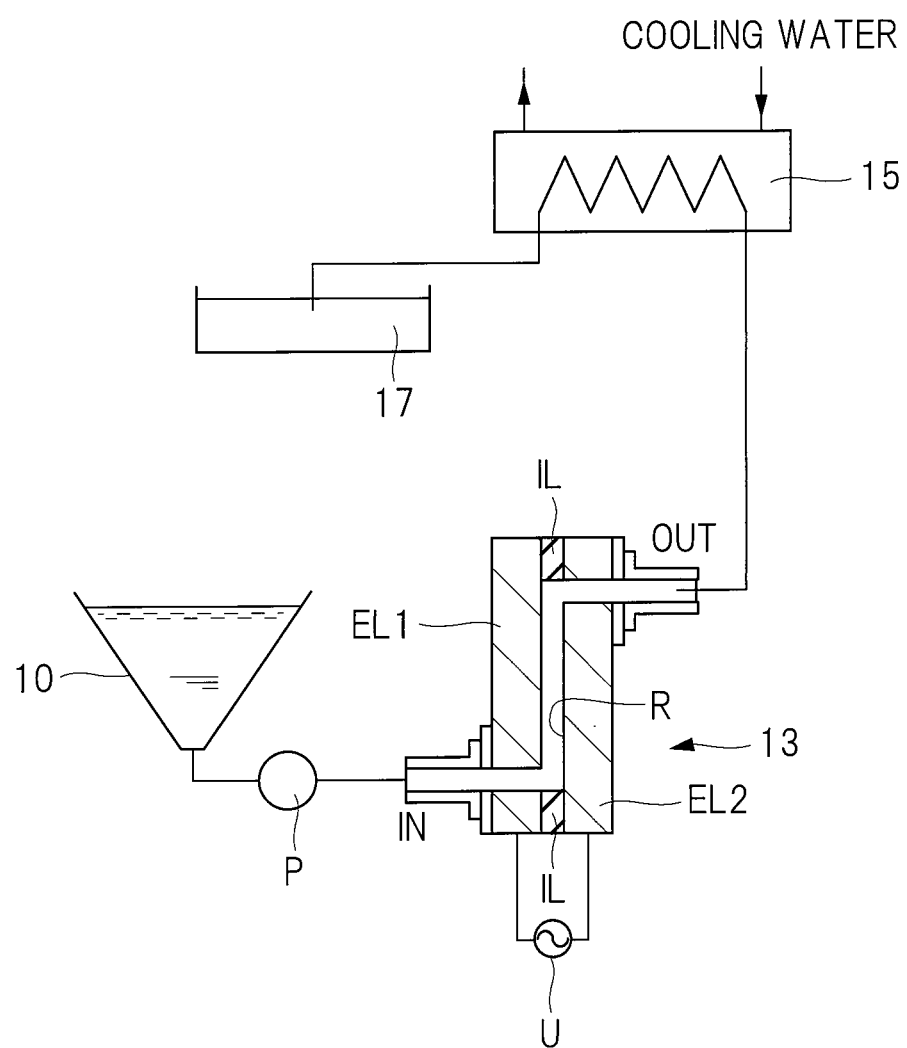
FIG. 8 is a diagram showing a device system for producing a yeast extract (high electric field treatment system)

FIG. 8 is a diagram showing a device system for producing a yeast extract. The system shown in FIG. 8 includes a hopper 10 into which the suspension of yeast to be treated is poured, an electric field applying device 13 connected with the hopper 10 via a flow path, and the heat exchanger 15 connected with the electric field applying device 13 via the flow path. A pump P is connected between the hopper 10 and the electric field applying device 13.

The hopper 10 is a container with which the flow path described above is connected. In this hopper 10, a liquid for a suspension (for example, ion-exchange water) and yeast may be mixed together.

In the electric field applying device 13, the electrodes EL1 and EL2 are arranged facing each other with the flow path R interposed therebetween. The electrodes EL1 and EL2 are insulated by an insulator IL. A power unit U is connected between the electrodes EL1 and EL2, and a predetermined voltage can be applied between the electrodes EL1 and EL2. As a result, an electric field is applied to the suspension between the electrodes EL1 and EL2. In addition, an AC electric field having a predetermined frequency can be applied between the electrodes EL1 and EL2. The frequency can be adjusted, for example, in a range of 5 kHz to 20 kHz. Further, the gap between the electrodes EL1 and EL2 is, for example, substantially 0.1 to 8 mm, and a voltage of 3 V to 1000 V per 1-mm gap between the electrodes EL1 and EL2 can be applied.

Accordingly, the suspension of yeast flowing in from an inflow port IN passes through between the electrodes EL1 and EL2, the electric field treatment is applied to the suspension of yeast during which the suspension of yeast passes through between the electrodes, and the resultant suspension is discharged from an outflow port OUT. The suspension of yeast to which the electric field treatment has been applied is heated by the application of the electric field, and is cooled by the heat exchanger 15.

A configuration of the heat exchanger 15 is not limited, and in the heat exchanger 15, for example, by flowing cooling water around the outer periphery of a coil-shaped flow path, a temperature of the suspension in the flow path is adjusted.

The suspension cooled by passing through the heat exchanger 15 is, for example, poured into a pack, the pack is sealed, and then, placed into a thermostat bath 17. The suspension was incubated at a predetermined temperature for a predetermined period of time in the thermostat bath 17. The thermostat bath 17 becomes an autolyzing unit of yeast.

Specifically, a suspension of yeast at room temperature, in which commercially-available dry yeast has been suspended in water so as to be 5% (w/v), is poured into the hopper 10, and the suspension is transferred through the pump P, for example, at 100 L/h. During 0.03 second, which is the passage time when the suspension of yeast passes through between the electrodes EL1 and EL2 of electric field applying device 13, an electric field of 150 V/mm is applied. As a result, the temperature of the suspension of yeast is increased up to 54° C. After this, the suspension of yeast is cooled down to 7° C. by the heat exchanger, and the suspension is dispensed into plastic packs by 100 ml each, and the plastic packs are sealed. Each plastic pack is heated at 45° C. for zero to six hours in the thermostat bath 17.

As described above, a yeast extract can be efficiently produced from a suspension of yeast by using the system as shown in FIG. 8. That is, in the production of a yeast extract, the process can be performed in a short period of time and in a short process. In addition, in the production of a yeast extract, it becomes easy to control the conditions of the applied electric field, the temperature, and the like.

In the foregoing, the present invention has been concretely described based on the embodiments. However, it is needless to say that the present invention is not limited to the foregoing embodiments and various modifications and alterations can be made within the scope of the present invention.

For example, in Example 1 and the like, the suspension of yeast was left for six hours, and then, Tests A to E1 and E2 were conducted. However, this is for suppressing variation of the suspension and for comparing each test more accurately and is not indispensable. For example, immediately after adjustment of the suspension of yeast, the electric field treatment may be performed. It has been confirmed that the amount of amino acids is increased also by the electric field treatment immediately after adjustment of the suspension of yeast.

In addition, in Example 1 and the like, the suspension of yeast after the electric field treatment was incubated at 45° C. for six hours to perform autolysis of yeast, but the incubation temperature and the incubation time are not limited thereto. The incubation temperature can be appropriately adjusted to 64° C. or less. Further, as the incubation time increases, the amount of amino acids tends to increase, but even if the incubation time is zero hour, an increase in the amount of amino acids has been confirmed. Furthermore, as the incubation time increases from zero hour to six hours, the amount of amino acids increases.

In addition, in Example 1 and the like, as a liquid for suspending yeast, for example, an ion-exchange water was used, but another solvent may be used. Further, in order to adjust the conductivity of the suspension, a salt (for example, NaCl), sugar, or the like may be added to the suspension.

Fourth Embodiment

There is no limitation on a device used for the electric field treatment described in the first and the second embodiments, but for example, a device described below can be used.

Figure 9:
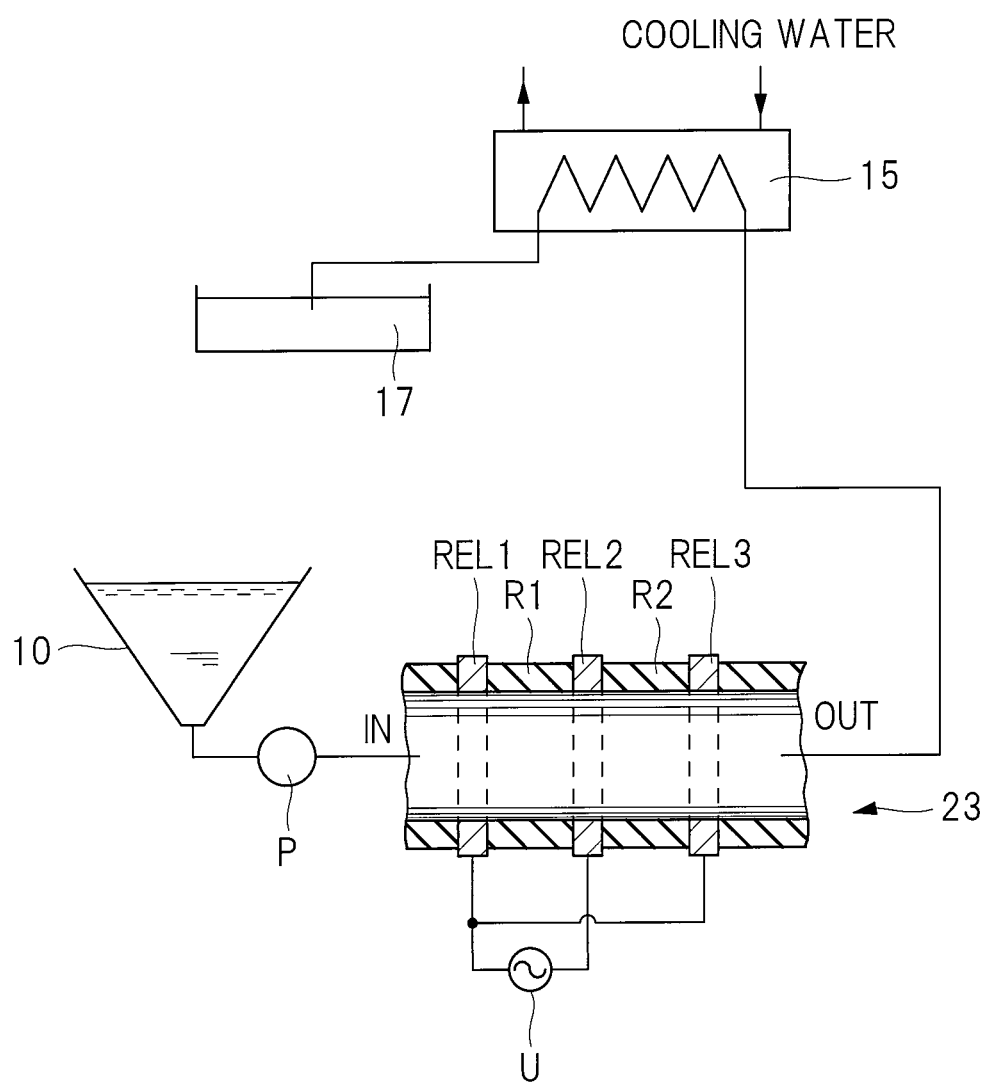
FIG. 9 is a diagram showing a device system for producing a yeast extract (low electric field treatment system)

FIG. 9 is a diagram showing a device system for producing a yeast extract. The system shown in FIG. 9 includes a hopper 10 into which the suspension of yeast to be treated is poured, an electric field applying device (electric field applying unit) 23 connected with the hopper 10 via a flow path, and the heat exchanger 15 connected with the electric field applying device 23 via the flow path. A pump P is connected between the hopper 10 and the electric field applying device 23.

The hopper 10 is a container with which the flow path described above is connected. In this hopper 10, a liquid for a suspension (for example, ion-exchange water) and yeast may be mixed together.

In the electric field applying device 23, ring electrodes (ring-shaped electrodes) REL1 and REL2 are arranged with a tube R1 interposed therebetween, and the ring electrode REL2 and a ring electrode REL3 are arranged with a tube R2 interposed therebetween. The tubes R1 and R2 are made of an insulating material. A power unit U is connected between the ring electrodes REL1 and REL2, and between the ring electrodes REL2 and REL3, and a predetermined electric field can be applied between the ring electrodes REL1 and REL2, and between the ring electrodes REL2 and REL3. In addition, an AC electric field having a predetermined frequency can be applied between the ring electrodes REL1 and REL2, and between the ring electrodes REL2 and REL3. The frequency can be adjusted, for example, in a range of 5 kHz to 100 kHz. Further, a gap (distance between the electrodes ED) between the ring electrodes REL1 and REL2, and between the ring electrodes REL2 and REL3 is, for example, substantially 75 mm, and a voltage of 1 V to 1000 V per 1-mm gap between the ring electrodes REL1 and REL2, and between the ring electrodes REL2 and REL3 can be applied. Each inner diameter of the tubes R1 and R2 and the ring electrodes REL1, REL2, and REL3 is, for example, substantially 17.5 mm.

Accordingly, the suspension of yeast flowing in from an inflow port IN passes through between the ring electrodes REL1 and REL3, the electric field treatment is applied to the suspension of yeast during which the suspension of yeast passes through between the electrodes, and the resultant suspension is discharged from an outflow port OUT. The suspension of yeast to which the electric field treatment has been applied is heated by the application of the electric field, and is cooled by the heat exchanger 15.

The configuration of the heat exchanger 15 is not limited, and in the heat exchanger 15, for example, by flowing cooling water around the outer periphery of a coil-shaped flow path, the temperature of the suspension in the flow path is adjusted.

The suspension cooled by passing through the heat exchanger 15 is, for example, poured into a pack, the pack is sealed, and then, placed into a thermostat bath 17. The suspension was incubated at a predetermined temperature for a predetermined period of time in the thermostat bath 17. The thermostat bath 17 is a unit autolyzing yeast.

Specifically, a suspension of yeast at room temperature, in which commercially-available dry yeast has been suspended in water so as to be 5% (w/v), is poured into the hopper 10, and the suspension is transferred through the pump P, for example, at 100 L/h. During 2.5 seconds, which is the passage time when the suspension of yeast passes through between the ring electrodes REL1 and REL3 of the electric field applying device 23, an electric field of 3 V/mm is applied. As a result, the temperature of the suspension of yeast is increased up to substantially 54° C. After this, the suspension of yeast is cooled down to 7° C. by the heat exchanger, and the suspension is dispensed into plastic packs by 100 ml each, and the plastic packs are sealed. Each plastic pack is heated at 45° C. for zero to six hours in the thermostat bath 17.

As described above, the yeast extract can be efficiently produced from the suspension of yeast by using the system as shown in FIG. 9. That is, in the production of the yeast extract, the process can be performed in a short period of time and in a short process. In addition, in the production of the yeast extract, it becomes easy to control the conditions of the applied electric field, the temperature, and the like. Note that three ring electrodes are used in the electric field applying device 23 described above, but two ring electrodes may be used, or three or more (for example, five) ring electrodes may be used.

FIG. 10 is a diagram summarizing an example of use conditions of the devices described in the third embodiment and the present embodiment. For example, the device in the third embodiment (FIG. 8) is suitable for the high electric field treatment (Test A) described in the first embodiment, and the device in the fourth embodiment (FIG. 9) is suitable for the low electric field treatment (Test E2) described in the first embodiment.

Although overlapping with the above descriptions of Test A and Test E2, an example of use conditions of the device of the third embodiment (high electric field treatment device in FIG. 8), and the device of the fourth embodiment (low electric field treatment device in FIG. 9) will be described with reference to FIG. 10.

As shown in FIG. 10, an electrode material of the high electric field treatment device and the low electric field treatment device is, for example, Ti. In addition to Ti, Pt may be used. Further, an electrode in which Ti is coated with Pt may be used.

With regard to a size of the flow path (electric field treatment unit) provided with electrodes, a longitudinal-section of the flow path is a substantially rectangular shape of substantially 6 mm×2 mm in the high electric field treatment device, and a length (RD) is 32 mm. Further, in the low electric field treatment device, a longitudinal-section of the flow path is a circular shape having a diameter of 17.5 mm, and a length (ED×2) is 75 mm×2.

In the high electric field treatment device, the distance between the electrodes is small (4 mm in this case), and by setting the voltage between the electrodes to 600 V, a high electric field (150 V/mm in this case) can be applied. The electric field of the high electric field treatment can be adjusted in a range of 50 V/mm to 500 V/mm by adjusting the distance between the electrodes and the voltage between the electrodes.

In the low electric field treatment device, the distance between the electrodes is relatively large (75 mm in this case), and by setting the voltage between the electrodes to 225 V, a low electric field (3 V/mm in this case) can be applied. The electric field of the low electric field treatment can be adjusted in a range of 3 V/mm to 50 V/mm by adjusting the distance between the electrodes and the voltage between the electrodes.

In both of the high electric field treatment device and the low electric field treatment device, an AC electric field is applied. That is, the positive and the negative of the voltage between the electrodes are switched at predetermined intervals. The frequency is, for example, 20 kHz. As the frequency, a frequency in a range of 5 kHz to 100 kHz is preferred. When the frequency is less than 5 kHz, degradation of the electrodes in quality due to electrolysis is easily generated, and the electrode maintenance becomes more frequent. In particular, in the high electric field treatment device and the low electric field treatment device described above, in-line treatment is required, cleaning and replacement of the electrodes are accompanied by decomposition of the device (electric field applying device), and the treatment efficiency is decreased. Further, as for the frequency, when the frequency exceeds 100 kHz, loss of power becomes large, and production costs become high.

Electric field application time (treatment time) is a time for which the treatment material (suspension of yeast) flows between the electrodes, and is, for example, a region where the electrodes face each other (length RD, substantially 32 mm in this case) in the high electric field treatment device. The treatment material passes through the region, for example, in substantially 0.03 second by pressing the pump. Further, in the low electric field treatment device, for example, the electric field application time is a distance between the electrodes (2×ED, substantially 2×75=150 mm in this case), and the treatment material passes through the distance, for example, in substantially 2.5 seconds by pressing the pump.

The electric field application time (treatment time) can be adjusted by the size of the flow path (electric field treatment unit) provided with the electrodes, or the pump pressure. For example, in the high electric field treatment device, the electric field application time (treatment time, or passage time in the electric field applying unit) can be adjusted in a range of 0.001 second or more to one second or less. Further, in the low electric field treatment device, the electric field application time (treatment time, or passage time in the electric field applying unit) can be adjusted in a range of one second or more to 30 seconds or less.

As described above, in the high electric field treatment device, the longitudinal-section of the flow path (electric field treatment unit) provided with the electrodes is small, and the high electric field treatment device is suitable for the treatment for a material having a low viscosity. The high electric field treatment device is suitable for the treatment for the one having a viscosity lower than that of, for example, tomato juice (viscosity: substantially 50 mPa·s) as a reference of the viscosity. In a case of a suspension of yeast, the high electric field treatment device is suitable for the treatment for the one, for example, with 13% (w/v) or less. In the low electric field treatment device, the longitudinal-section of the flow path (electric field treatment unit) provided with the electrodes is large, and the low electric field treatment device is suitable also for the treatment for a material having a high viscosity. The low electric field treatment device can perform the treatment also for the one having a high viscosity, for example, a sweet bean paste (viscosity: 1000000 mPa·s or more) as a reference of the viscosity. For example, it is preferred that the suspension of yeast with 13% (w/v) or more is treated by the low electric field treatment device.

The suspension of yeast used in Tests A and E2 is substantially 5%, and can be treated by the high electric field treatment device or also by the low electric field treatment device. In addition, by increasing the concentration of the suspension of yeast, the treatment efficiency can be improved. As described above, in a case where the viscosity is increased, the low electric field treatment device is preferably used.

As described above, by applying the electric field treatment to the suspension of yeast with the high electric field treatment device or the low electric field treatment device described above, the yeast extract can be efficiently produced. That is, in the production of the yeast extract, the process can be performed in a short period of time and in a short process. In addition, in the production of the yeast extract, it becomes easy to control the conditions of the applied electric field and the like.

Fifth Embodiment

In the present embodiment, an influence of the incubation time on the autolysis rate of yeast will be described.

Example 5

With regard to the influence of the incubation time on the autolysis rate of yeast, the following Tests F1, F2, G1, and G2 were conducted and examined.

(Test F1)

Commercially-available dry yeast (*Saccharomyces cerevisiae*) was suspended in ion-exchanged water at a final concentration of 5% (w/v). After standing for six hours, the suspension of yeast was used for electric field treatment. Next, a high electric field (high AC electric field) of 20 kHz and 500 V/mm was applied for 0.03 s to the obtained suspension of yeast. Application time of this high electric field corresponds to passage time of the suspension between the electrodes. Specifically, the suspension was allowed to pass through between the electrodes having a 4-mm gap between the electrodes, a voltage of 2000 V was applied between the electrodes, and the suspension was allowed to pass through between the electrodes in 0.03 s. The temperature of the suspension was increased up to 54° C. with the application of the electric field. This suspension was cooled down to 7° C. with the heat exchanger, and then, the cooled suspension was incubated at 45° C. for zero to 24 hours to perform autolysis of yeast. That is, the incubation time was set in the range of zero to 24 hours. Since the weight of the cells decreases with the lapse of time due to the autolysis, yeast cells contained in a certain amount of suspension were recovered by centrifugation, the dry weight (insoluble fraction amount) of the yeast cells was determined, and from the ratio of the reduced weight, an autolysis rate [(dried cell weight at zero hour−dried cell weight after treatment/dried cell weight at zero hour)×100%] was determined. Note that the dried cell weight at zero hour is the amount of insoluble fraction at start-up, and further, the dried cell weight after treatment is the amount of insoluble fraction at the time of the measurement.

The suspension of yeast (yeast liquid) after autolysis was heated to 80° C. to inactivate the yeast. After that, free amino acid analysis in the yeast liquid was performed.

In addition, as a control, commercially-available dry yeast was suspended in water so as to be 5% (w/v), and the resultant mixture was left for six hours to obtain a suspension of the yeast. The obtained suspension was incubated at 45° C. for zero to 24 hours to perform autolysis of yeast without applying an electric field. The suspension of yeast (yeast liquid) after the autolysis was heated at 80° C. to stop the yeast reaction. After that, the autolysis rate was determined.

In addition, as a comparison test, commercially-available dry yeast was suspended in water so as to be 5% (w/v), and ethyl acetate was added to the suspension so as to be 3.3 ml/L as a chemical to promote the autolysis of yeast, and then, the resultant mixture was left for six hours to obtain the suspension of the yeast. The obtained suspension was incubated at 45° C. for zero to 24 hours to perform the autolysis of yeast without applying an electric field. The suspension of yeast (yeast liquid) after the autolysis was heated at 80° C. to stop the yeast reaction. After that, the autolysis rate was determined.

Figure 11A:
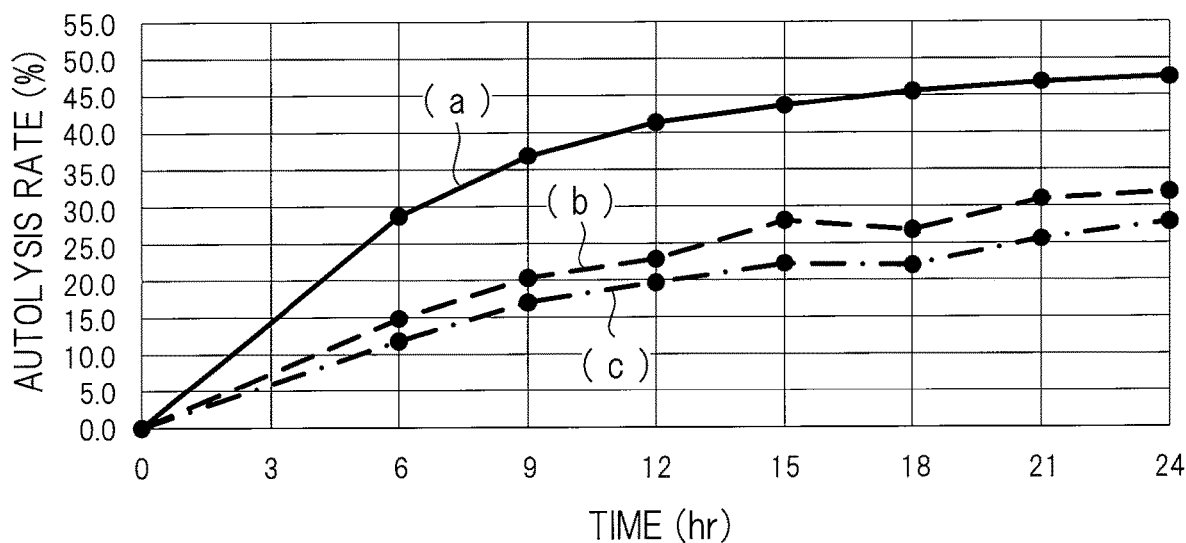
FIG. 11A is a graph showing the relation between the autolysis rate and the incubation time of yeast (dry yeast)

FIG. 11A is a graph showing the relation between the autolysis rate and the incubation time of yeast (dry yeast). A graph (a) shows the results in the case of the high electric field treatment for dry yeast, a graph (b) shows the results in the case of adding ethyl acetate, and a graph (c) shows the results in the case of a control. The horizontal axis is the incubation time (hr), and the vertical axis is the autolysis rate (%).

As shown in FIG. 11A, in the high electric field treatment for dry yeast, the autolysis rate was higher than that in the case of adding ethyl acetate at any incubation time. In particular, the autolysis rate is rapidly increased in the graph (a), and a high autolysis rate of 25% or more was obtained even when the incubation time was substantially six hours.

(Test F2)

Figure 11B:
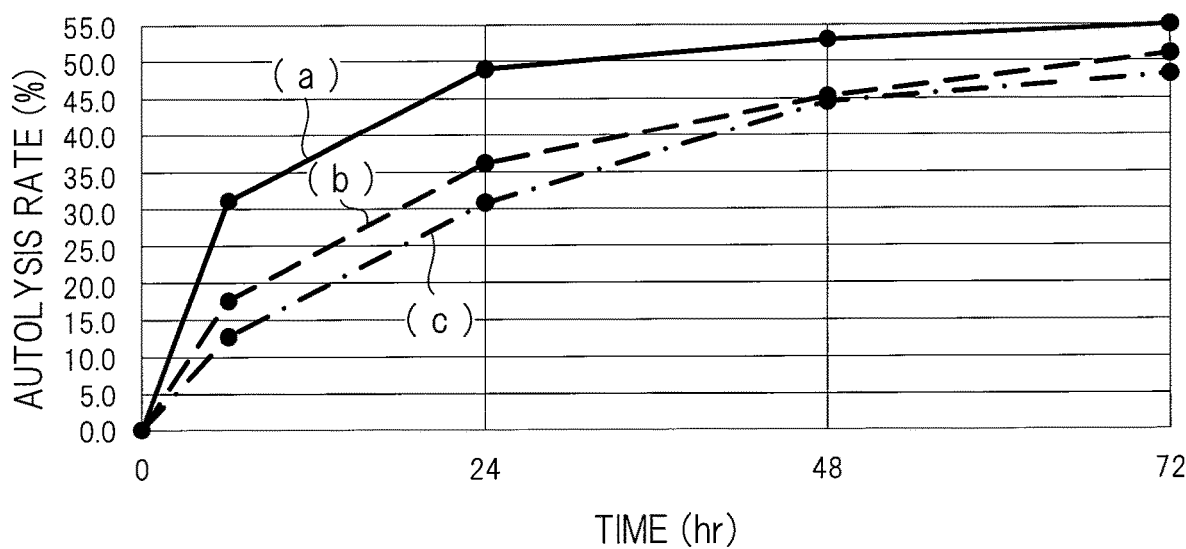
FIG. 11B is a graph showing the relation between the autolysis rate and the incubation time of yeast (dry yeast)

Further, the incubation time was set in a range of zero to 72 hours, which is longer than a range of zero to 24 hours in Test F1, and the test was performed in the similar manner as in Test F1. FIG. 11B is a graph showing the relation between the autolysis rate and the incubation time of yeast (dry yeast). A graph (a) shows the results in the case of the high electric field treatment for dry yeast, a graph (b) shows the results in the case of adding ethyl acetate, and a graph (c) shows the results in the case of a control. The horizontal axis is the incubation time (hr), and the vertical axis is the autolysis rate (%).

As shown in FIG. 11B, in the high electric field treatment for dry yeast, the autolysis rate became substantially 50% when the incubation time was substantially 24 hours. Note that the reach value of the autolysis rate of the common yeast is considered to be substantially 50%.

(Test G1)

The test was performed in the similar manner as in Test F1 by replacing the dry yeast (dried yeast) with fresh yeast (compressed yeast).

Figure 12A:
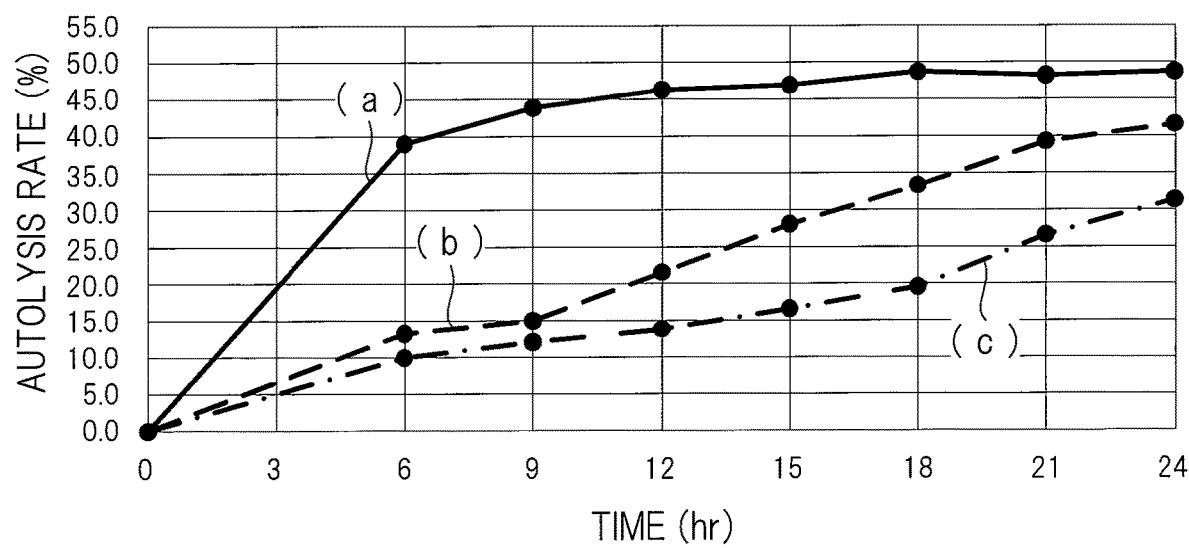
FIG. 12A is a graph showing the relation between the autolysis rate and the incubation time of yeast (fresh yeast)

FIG. 12A is a graph showing the relation between the autolysis rate and the incubation time of yeast (fresh yeast). A graph (a) shows the results in the case of the high electric field treatment for fresh yeast, a graph (b) shows the results in the case of adding ethyl acetate, and a graph (c) shows the results in the case of a control.

As shown in FIG. 12A, in the high electric field treatment for fresh yeast, the autolysis rate was higher than that in the case of adding ethyl acetate at any incubation time. In particular, the autolysis rate is rapidly increased in the graph (a), and a satisfactory autolysis rate was obtained even when the incubation time was substantially six hours.

(Test G2)

Figure 12B:
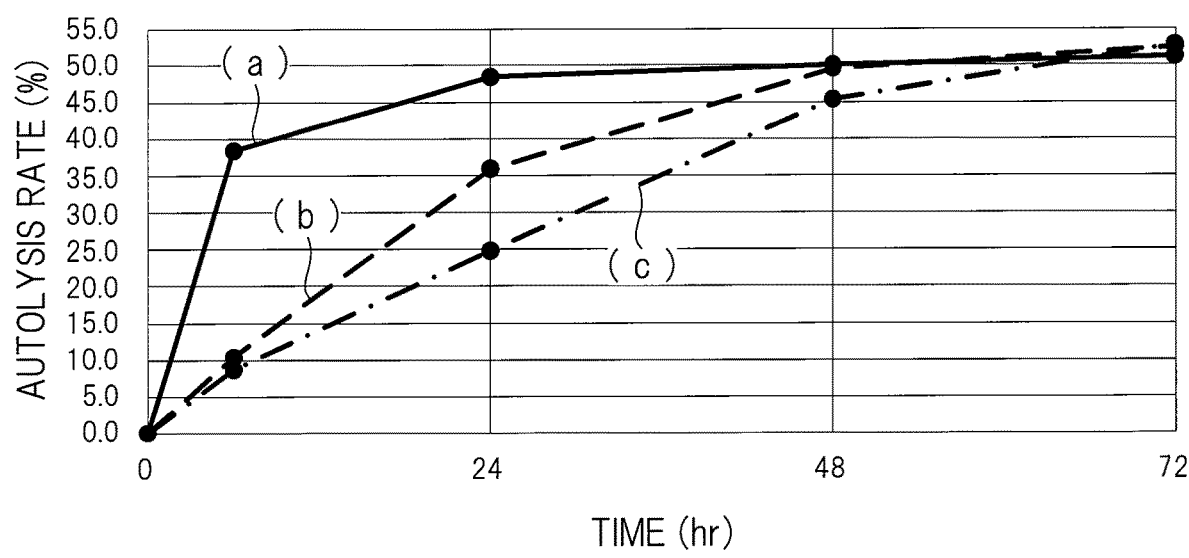
FIG. 12B is a graph showing the relation between the autolysis rate and the incubation time of yeast (fresh yeast)

Further, the incubation time was set in the range of zero to 72 hours, which is longer than the range of zero to 24 hours in Test G1, and the test was performed in the similar manner as in Test G1. FIG. 12B is a graph showing the relation between the autolysis rate and the incubation time of yeast (fresh yeast). A graph (a) shows the results in the case of the high electric field treatment for fresh yeast, a graph (b) shows the results in the case of adding ethyl acetate, and a graph (c) shows the results in the case of a control. The horizontal axis is the incubation time (hr), and the vertical axis is the autolysis rate (%).

As shown in FIG. 12B, in the high electric field treatment for fresh yeast, the autolysis rate became substantially 50% when the incubation time was substantially 24 hours.

(Regarding Results of Free Amino Acid Analysis of Tests F2 and G2)

The results of free amino acid analysis of Tests F2 and G2 described above will be described below with reference to FIGS. 13A to 16B.

Figure 13A:
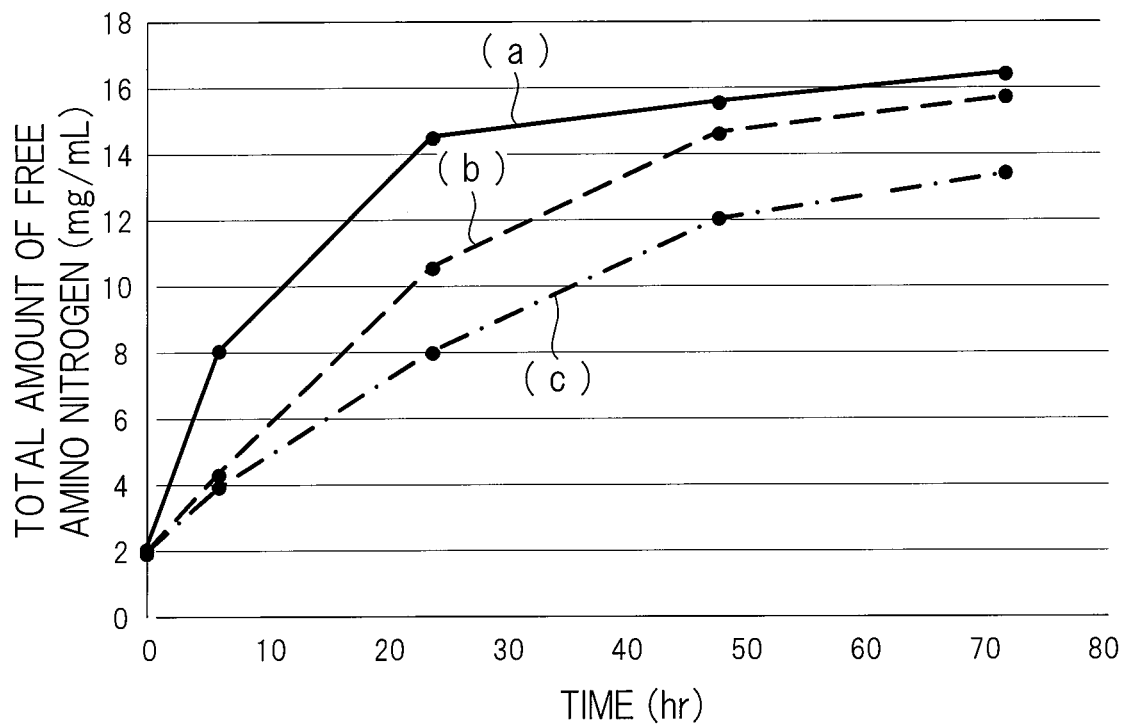
FIG. 13A is a graph showing a total amount of free amino nitrogen in Test F2.
Figure 13B:
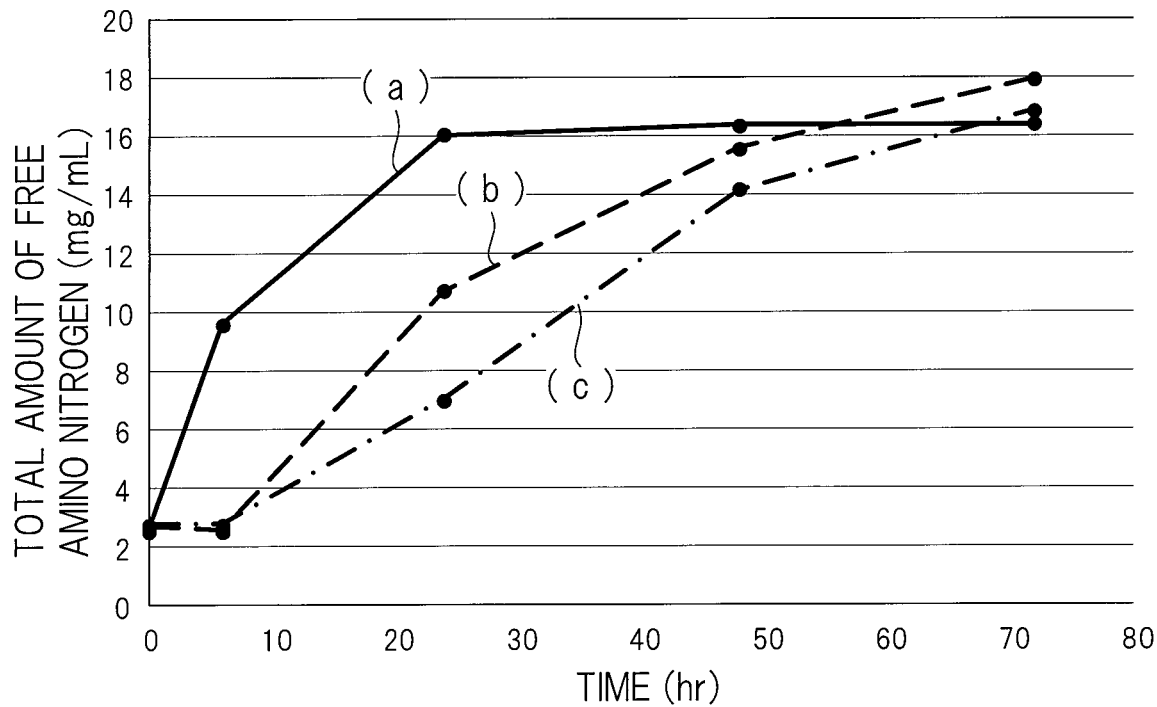
FIG. 13B is a graph showing a total amount of free amino nitrogen in Test G2.
Figure 14A:
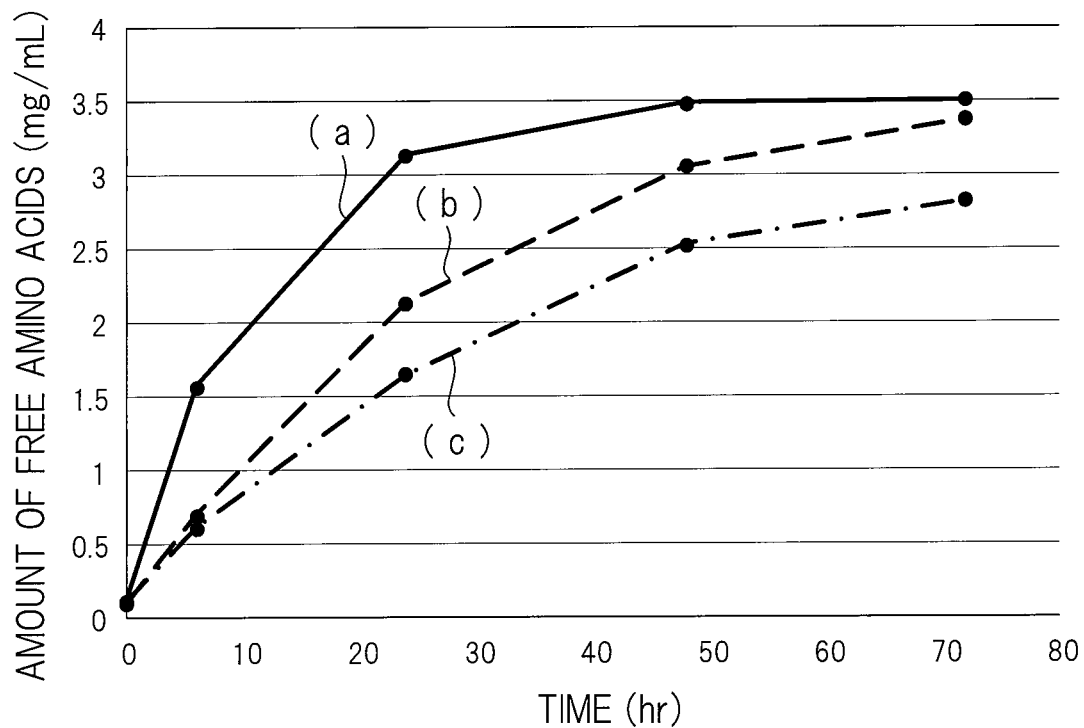
FIG. 14A is a graph showing an amount of branched chain amino acids in Test F2.
Figure 14B:
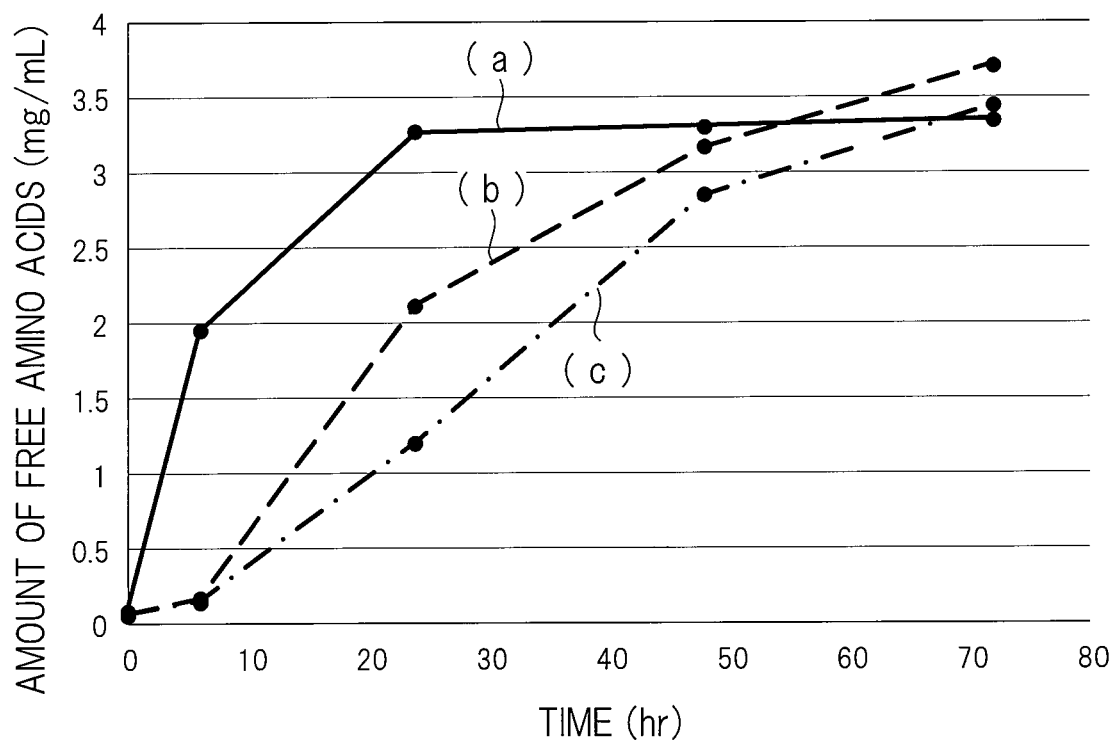
FIG. 14B is a graph showing an amount of branched chain amino acids in Test G2.
Figure 15A:
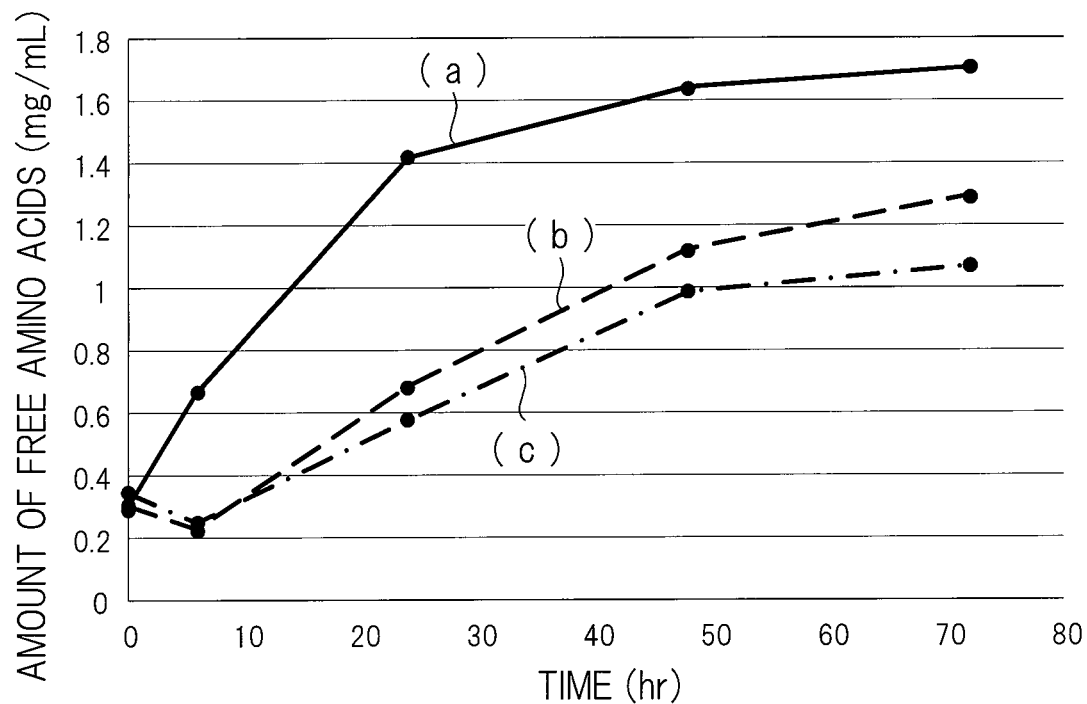
FIG. 15A is a graph showing an amount of glutamic acid in Test F2.
Figure 15B:
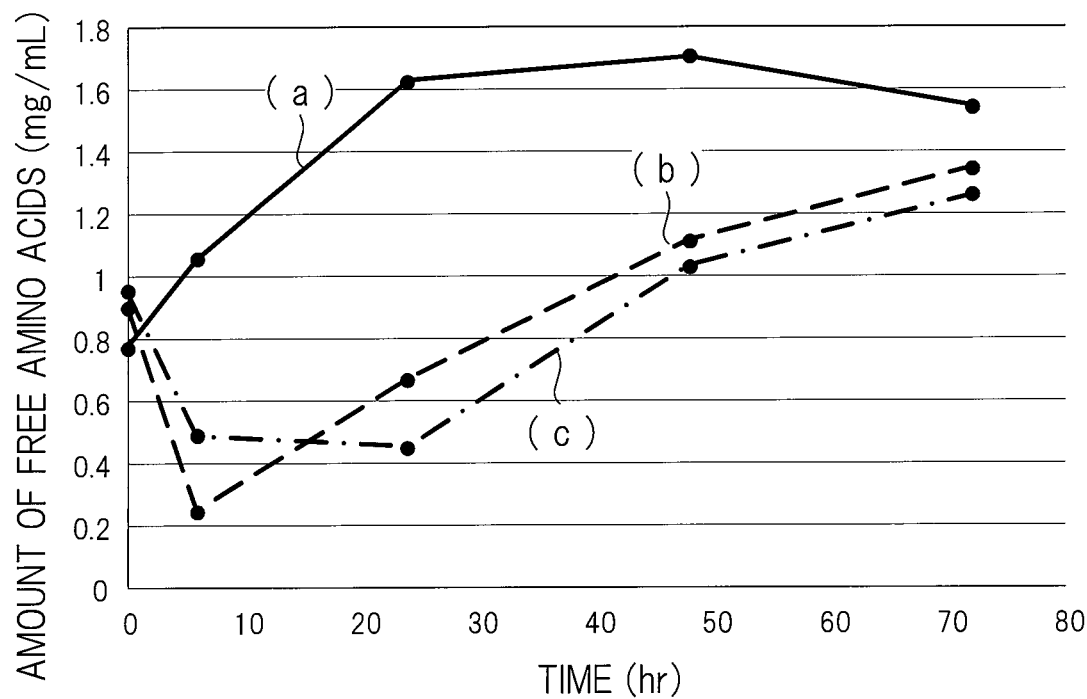
FIG. 15B is a graph showing an amount of glutamic acid in Test G2.
Figure 16A:
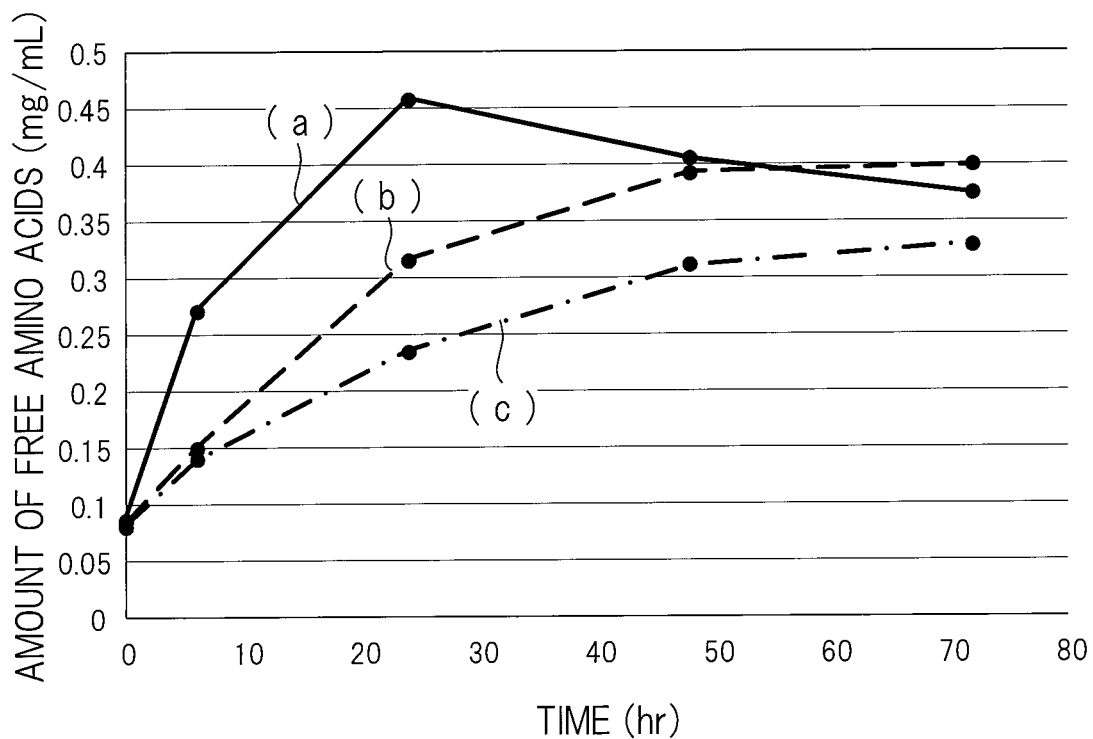
FIG. 16A is a graph showing an amount of glutamine in Test F2.
Figure 16B:
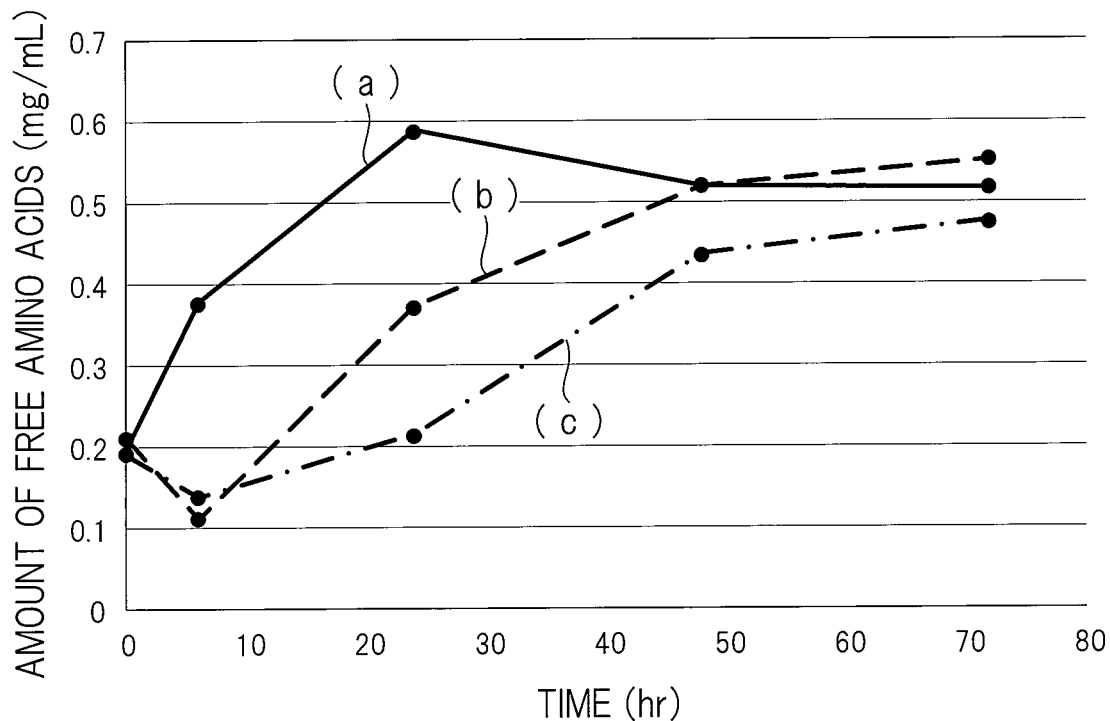
FIG. 16B is a graph showing an amount of glutamine in Test G2.

FIG. 13A is a graph showing a total amount of free amino nitrogen in Test F2, and FIG. 13B is a graph showing a total amount of free amino nitrogen in Test G2. FIG. 14A is a graph showing an amount of branched chain amino acids in Test F2, and FIG. 14B is a graph showing an amount of branched chain amino acids in Test G2. FIG. 15A is a graph showing an amount of glutamic acid in Test F2, and FIG. 15B is a graph showing an amount of glutamic acid in Test G2. FIG. 16A is a graph showing an amount of glutamine in Test F2, and FIG. 16B is a graph showing an amount of glutamine in Test G2. In any one of the drawings, FIGS. 13A, 14A, 15A, and 16A show the results in the case of Test F2 (dry yeast), and FIGS. 13B, 14B, 15B, and 16B show the results in the case of Test G2 (fresh yeast). Further, in each drawing, a graph (a) shows the results in the case of the high electric field treatment, a graph (b) shows the results in the case of adding ethyl acetate, and a graph (c) shows the results in the case of a control.

In FIGS. 13A and 13B, the horizontal axis is the incubation time (hr), and the vertical axis is the total amount of free amino nitrogen (mg/mL). As shown in FIGS. 13A and 13B, in both cases of the dry yeast of FIG. 13A and the fresh yeast of FIG. 13B, in the case of the high electric field treatment of the graph (a), a rapid increase in the total amount of free amino nitrogen was able to be confirmed. In particular, as compared with the case of adding ethyl acetate of the graph (b), an increase in the total amount of free amino nitrogen in a short incubation time was able to be confirmed.

In FIGS. 14A and 14B, the horizontal axis is the incubation time (hr), and the vertical axis is the amount of branched chain amino acids (amount of free amino acids (mg/mL)). As shown in FIGS. 14A and 14B, in both cases of the dry yeast of FIG. 14A and the fresh yeast of FIG. 14B, in the case of the high electric field treatment of the graph (a), a rapid increase in the amount of branched chain amino acids (amount of free amino acids) was able to be confirmed. In particular, as compared with the case of adding ethyl acetate of the graph (b), an increase in the amount of branched chain amino acids (amount of free amino acids) in a short incubation time was able to be confirmed.

In FIGS. 15A and 15B, the horizontal axis is the incubation time (hr), and the vertical axis is the amount of glutamic acid (amount of free amino acids (mg/mL)). Glutamic acid is one kind of the amino acids having umami taste. As shown in FIGS. 15A and 15B, in both cases of the dry yeast of FIG. 15A and the fresh yeast of FIG. 15B, in the case of the high electric field treatment of the graph (a), a rapid increase in the amount of glutamic acid (amount of free amino acids) was able to be confirmed. In particular, as compared with the case of adding ethyl acetate of the graph (b), an increase in the amount of glutamic acid (amount of free amino acids) in a short incubation time was able to be confirmed.

In FIGS. 16A and 16B, the horizontal axis is the incubation time (hr), and the vertical axis is the amount of glutamine (amount of free amino acids (mg/mL)). As shown in FIGS. 16A and 16B, in both cases of the dry yeast of FIG. 16A and the fresh yeast of FIG. 16B, in the case of the high electric field treatment of the graph (a), a rapid increase in the amount of glutamine (amount of free amino acids) was able to be confirmed. In particular, as compared with the case of adding ethyl acetate of the graph (b), an increase in the amount of glutamine (amount of free amino acids) in a short incubation time was able to be confirmed.

In the foregoing, the invention made by the inventors of the present invention has been concretely described based on the embodiments. However, it is needless to say that the present invention is not limited to the foregoing embodiments and various modifications and alterations can be made within the scope of the present invention.

For example, in Example 1 and the like, the suspension of yeast was left for six hours, and then, Tests A to E1, and E2 were conducted. However, this is for suppressing variation of the suspension and for comparing each test more accurately and is not indispensable. For example, immediately after adjustment of the suspension of yeast, the electric field treatment may be performed. It has been confirmed that the amount of amino acids is increased also by the electric field treatment immediately after adjustment of the suspension of yeast.

In addition, in Example 1 and the like, the suspension of yeast after the electric field treatment was incubated at 45° C. for six hours to perform autolysis of yeast, but the incubation temperature and the incubation time are not limited thereto. The incubation temperature can be appropriately adjusted to 64° C. or less. Further, as the incubation time increases, the amount of amino acids tends to increase, but even if the incubation time is zero hour, an increase in the amount of amino acids has been confirmed. Furthermore, as the incubation time increases from zero hour to six hours, the amount of amino acids increases.

In addition, in Example 1 and the like, as a liquid for suspending the yeast, for example, an ion-exchange water was used, but another solvent may be used. Further, in order to adjust a conductivity of the suspension, salts (for example, NaCl), sugar, or the like may be added to the suspension.

What is claimed is:

1. A method of producing a yeast extract, comprising the steps of:
   (a) preparing a suspension containing yeast;
   (b) applying an electric field treatment to the suspension; and
   (c) after the step (b), autolyzing the yeast in the suspension,
   wherein the step (b) is a step of applying a voltage to a first electrode and a second electrode while flowing the suspension continuously into an electric field applying unit having the first electrode and the second electrode, the electrodes being arranged along a flow path so as to face each other, and
   in the step (b),
      the electric field to be applied is 50 V/mm or more to 150 V/mm or less, and
      a temperature of the suspension during an application period of the voltage is 64° C. or less;
   wherein the suspension flows in a direction parallel to a plane defined by the surface of the first electrode or the second electrode.

2. The method of producing a yeast extract according to claim 1,
   wherein, in the step (b),
   an application time of the voltage is less than 25 seconds.

3. The method of producing a yeast extract according to claim 2,
   wherein, in the step (b),
   a voltage to be applied is an AC voltage.

4. The method of producing a yeast extract according to claim 1, wherein the yeast is genus *Saccharomyces* or genus *Candida*.

5. The method of producing a yeast extract according to claim 1,
wherein the yeast is dry yeast or fresh yeast.

6. The method of producing a yeast extract according to claim 1,
wherein, in the step (b),
a voltage to be applied is an AC voltage having a frequency of 5 kHz or more to 100 kHz or less.

7. The method of producing a yeast extract according to claim 6,
wherein, in the step (b),
an application time of the AC voltage to the suspension is 0.001 second or more to one second or less.

8. The method of producing a yeast extract according to claim 6,
wherein, in the step (b),
the electrodes have a first electrode and a second electrode arranged facing each other, and
the suspension flows between the first electrode and the second electrode.

9. The method of producing a yeast extract according to claim 1,
wherein, in the step (b),
an application time of the AC voltage to the suspension is one second or more to 30 seconds or less.

10. A method of producing a yeast extract, comprising the steps of:
(a) preparing a suspension containing yeast;
(b) applying an electric field treatment to the suspension; and
(c) after the step (b), autolyzing the yeast in the suspension,
wherein the step (b) is a step of applying a voltage to a first ring electrode, a second ring electrode and a third ring electrode while flowing the suspension continuously into an electric field applying unit having an electric field applied between the first electrode and the second electrode and an electric field applied between the second electrode and the third electrode, the first ring electrode, the second ring electrode and the third ring electrode being fitted to an outer periphery of a flow path, and
in the step (b),
an electric field to be applied between each of the ring electrode pairs is 3 V/mm or more to 50 V/mm or less, and
a temperature of the suspension during an application period of the voltage is 64° C. or less;
wherein a first insulating tube is disposed between the first ring electrode and the second ring electrode, and a second insulating tube is disposed between the second ring electrode and the third ring electrode; and
wherein the flow path between the first ring electrode and the third ring electrode has a constant cross-section.

11. The method of producing a yeast extract according to claim 10,
wherein, in the step (b),
a voltage to be applied is an AC voltage having a frequency of 5 kHz or more to 100 kHz or less.

12. The method of producing a yeast extract according to claim 11,
wherein, in the step (b),
an application time of the AC voltage to the suspension is one second or more to 30 seconds or less.

13. The method of producing a yeast extract according to claim 10,
wherein the yeast is genus *Saccharomyces* or genus *Candida*.

14. The method of producing a yeast extract according to claim 10,
wherein the yeast is dry yeast or fresh yeast.

* * * * *